(12) United States Patent
McCord et al.

(10) Patent No.: US 10,344,323 B1
(45) Date of Patent: Jul. 9, 2019

(54) CPG SITES DIFFERENTIALLY METHYLATED IN SMOKERS AND NON-SMOKERS

(71) Applicants: Bruce McCord, Miami, FL (US); Hussain Alghanim, Miami, FL (US)

(72) Inventors: Bruce McCord, Miami, FL (US); Hussain Alghanim, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/900,321

(22) Filed: Feb. 20, 2018

(51) Int. Cl.
  C07H 21/04 (2006.01)
  C12Q 1/68 (2018.01)
  C12Q 1/686 (2018.01)
  G01N 33/49 (2006.01)
  C07K 14/47 (2006.01)
  C12Q 1/6844 (2018.01)

(52) U.S. Cl.
  CPC .......... *C12Q 1/686* (2013.01); *C07K 14/4702* (2013.01); *C12Q 1/6844* (2013.01); *G01N 33/49* (2013.01); *C12Q 2600/154* (2013.01)

(58) Field of Classification Search
  None
  See application file for complete search history.

(56) References Cited

U.S. PATENT DOCUMENTS

| | | |
|---|---|---|
| 2012/0108444 A1 | 5/2012 | Philibert et al. |
| 2013/0150255 A1 | 6/2013 | Murrelle et al. |
| 2016/0289768 A1 | 10/2016 | Laird et al. |
| 2017/0183728 A1 | 6/2017 | Philibert et al. |

OTHER PUBLICATIONS

Tian et al. (Placenta, vol. 52, pp. 49-57, Apr. 30, 2017). (Year: 2017).*
Lee et al. (PLOS Once, vol. 12 No. 4, e0176783,Apr. 28, 2017, 12 pages). (Year: 2017).*
Endo et al. (Hindawi Publishing Corporation, BioMed Research International, vol. 2015, Article ID 451981, 10 pages). (Year: 2015).*
Adams et al. (Cancer Prevention Res, vol. 1, No. 5, pp. 357-361, 2008). (Year: 2008).*
NEB catalog (1998/1999), pp. 121, 284 (Year: 1998).*
Alghanim, H. et al., "Detection and evaluation of DNA methylation markers found at SCGN and KLF14 loci to estimate human age." Forensic Science Internaonal: Genetics, 2017, 31: 81-88.
Anderson, A. M. et al., "Current and Future Prospects for Epigenetic Biomarkers of Substance Use Disorders." Genes, 2015, 6: 991-1022.
Bauer, M. et al., "Tobacco smoking differently influences cell types of the innate and adaptive immune system—indications from CpG site methylation." Clinical Epigenetics, 2016, 8 (83): 1-12.
Bossé, Y. et al., "Molecular Signature of Smoking in Human Lung Tissues." Cancer Res., 2012, 72: 3753-3763.
Breitling, L. P. et al., "Tobacco-Smoking-Related Differential DNA Methylation: 27K Discovery and Replication." The American Journal of Human Genetics, Apr. 2011, 88: 450-457.
Dogan, M. V. et al., "The effect of smoking on DNA methylation of peripheral blood mononuclear cells from African American women." BMC Genomics, 2014, 15 (151): 1-13.
Elliott, H. R. et al., "Differences in smoking associated DNA methylation patterns in South Asians and Europeans." Clinical Epigenetics, 2014, 6 (4): 1-10.
Endo, K. et al., "Establishment of the MethyLight Assay for Assessing Aging, Cigarette Smoking, and Alcohol Consumption." BioMed Research International, 2015, 2015 (451981): 1-10.
Evans, B. R. et al., "Repression of Aryl Hydrocarbon Receptor (AHR) Signaling by AHR Repressor Role of DNA Binding and Competition for AHR Nuclear Translocator" Mol. Pharmacol., Feb. 2008, 73 (2): 387-398.
Fraga, M. F. et al., "Epigenetic differences arise during the lifetime of monozygotic twins." PNAS, Jul. 2005, 102 (30): 10604-10609.
Joubert, B. R. et al., "450K Epigenome-Wide Scan Identifies Differential DNA Methylation in Newborns Related to Maternal Smoking during Pregnancy." Environmental Health Perspectives, Oct. 2012, 120 (10): 1425-1432.
Lee, K. W. K., Pausova, Z., "Cigarette smoking and DNA methylation." Frontiers in Genetics, Jul. 2013, 4 (132): 1-11.
Madi, T. et al., "The determination of tissue-specific DNA methylation patterns in forensic biofluids using bisulfite modification and pyrosequencing." Electrophoresis, 2012, 33: 1736-1745.
Monick, M. M. et al., "Coordinated Changes in AHRR Methylation in Lymphoblasts and Pulmonary Macrophages from Smokers." American Journal of Medical Genetics Part B, 2011, 141-151.
Philibert, R. et al., "A quantitative epigenetic approach for the assessment of cigarette consumption." Frontiers in Psychology, Jun. 2015, 6 (656): 1-8.
Shenker, N. S. et al., "DNA Methylation as a Long-term Biomarker of Exposure to Tobacco Smoke." Epidemiology, Sep. 2013, 24 (5): 712-716.
Shenker, N. S. et al., "Epigenome-wide association study in the European Prospective Investigation into Cancer and Nutrition (EPIC-Turin) identifies novel genetic loci associated with smoking." Human Molecular Genetics, 2013, 22 (5): 843-851.
Tsaprouni, L. G. et al., "Cigarette smoking reduces DNA methylation levels at multiple genomic loci but the effect is partially reversible upon cessation." Epigenetics, Oct. 2014, 9 (10): 1382-1396.

(Continued)

*Primary Examiner* — Jeanine A Goldberg
(74) *Attorney, Agent, or Firm* — Saliwanchik, Lloyd & Eisenschenk

(57) ABSTRACT

The subject invention pertains to biomarkers for identifying the source of a cell as a current, former, or never smoker. In certain embodiments, the methylation status at the AHRR locus in the genomic DNA isolated from a cell is determined by pyrosequencing technique using specific primers described herein. Kits containing primers and reagents for carrying out the methods disclosed herein are also provided.

22 Claims, 2 Drawing Sheets
Specification includes a Sequence Listing.

(56) References Cited

OTHER PUBLICATIONS

Wan, E S. et al., "Cigarette smoking behaviors and time since quitting are associated with differential DNA methylation across the human genome." Human Molecular Genetics, 2012, 21 (13): 3073-3082.

Warnecke, P. M. et al., "Identification and resolution of artifacts in bisulfite sequencing." Methods, 2002, 27: 101-107.

Zeilinger, S. et al., "Tobacco Smoking Leads to Extensive Genome-Wide Changes in DNA Methylation." PLOS One, May 2013, 8 (5): 1-14.

Zhang, Y. et al., "Smoking-associated DNA methylation markers predict lung cancer incidence." Clinical Epigenetics, 2016, 8 (127): 1-12.

* cited by examiner

CPG SITES DIFFERENTIALLY METHYLATED IN SMOKERS AND NON-SMOKERS

SEQUENCE LISTING

The Sequence Listing for this application is labeled "SeqList-ST25," which was created on Feb. 15, 2018, and is 13 KB. The Sequence Listing is incorporated herein by reference in its entirety.

BACKGROUND OF THE INVENTION

DNA methylation is one of the epigenetic mechanisms for gene regulation. Variations in DNA methylation status in certain loci control gene expression by silencing or activating specific genes. The presence of a methyl group on the 5' carbon of a cytosine belonging to the dinucleotide CG (CpG) is believed to prevent the binding of the transcription machinery in the promoter of a gene. Some loci on the genome called "tissue-specific differentially methylated regions" (tDMRs) can therefore be used for cell identification because they present different DNA methylation status across different cell types. To determine the pattern of DNA methylation at a locus, the most commonly used methods include the bisulfite modification of genomic DNA. The bisulfite chemically converts the unmethylated cytosines to uracils but does not react with methylated cytosines. During a polymerase chain reaction (PCR) the uracils get copied as thymines and the amplicons can then be sequenced to determine the presence of a cytosine or a thymine at each specific CpG.

Generally, DNA methylation occurs through methylation of cytosine residues in the CpG dinucleotide sites by DNA methyl transferases (DNMT). The methylation process can inhibit gene transcription by recruitment of chromatin remodeling factors that influence the accessibility of DNA during transcription.

Environmental factors play an important role in modifying the DNA methylation status at certain sites. For example, differences in DNA methylation status in monozygotic twins are greater for the pairs that spend less of their lifetime together or exhibit different lifestyles. Environmental exposures such as diet, stress, and smoking can alter DNA methylation at various stages of human development.

Tobacco smoking is a powerful environmental factor that changes DNA methylation. Changes in DNA methylation can mediate the effects of tobacco smoking in people which can affect gene expression in certain genetic loci. Tobacco smoking can alter DNA methylation through several mechanisms. First, smoking can modulate methylation patterns through carcinogen-induced DNA damage and repair. Various carcinogenic materials in tobacco, particularly cigarettes, such as arsenic, nitrosamines, polycyclic aromatic hydrocarbons, and formaldehyde can cause double-stranded DNA breaks. Such breaks require DNA repair which is mediated by DNA methyltransferase 1 (DNMT1) to methylate the CpGs adjacent to the repaired sites. Smoking can also alter DNA methylation status though a nicotine effect on gene expression. Nicotine has the ability to alter DNMT1 activity and affect protein expression. Third, smoking can modify DNA methylation by affecting the expression and activity of DNA-binding factors such as Sp1. Smoking increases Sp1 expression which binds to GC-rich motifs in gene promoters and subsequently to prevent de novo methylation of CpGs at these motifs. Hypoxia is another mechanism by which tobacco smoking may alter DNA methylation. Tobacco smoke contains carbon monoxide that binds to hemoglobin and reduces the oxygen levels in the tissue. In turn, hypoxia may upregulate methionine adenosyltransferase 2A that is responsible for S-adenosylmethionine synthesis, a key methyl donor for any DNA methylation. Thus, variation in DNA methylation is one mechanism that can potentially mediate the effects of tobacco smoking.

Techniques to distinguish current smokers from never smokers based on DNA methylation status are not established. The majority of techniques to determine DNA methylation to distinguish current smokers from never smokers developed so far are based on chip arrays that only provide information on a single CpG site. In addition, the array studies require large amounts of DNA and laborious bioinformatic analysis which may not be suitable for forensic or other applications with limited samples. On the other hand, the pyrosequencing-based technique permits identification and quantification of the methylation status of clusters of CpG sites associated with a genomic locus. Pyrosequencing allows highly accurate determination of methylation status at each CpG site within a genomic locus. Further, this technique utilizes a minimal amount of starting DNA material which permits downstream short tandom repeat (STR) testing as well.

A variety of chip array-based platforms (e.g. Illumina 27K and 450K) have been developed to permit a much broader investigation and identification of differentially methylated loci across the genome. Several genetic loci have appeared as robust indicators of tobacco smoking as a result of investigations utilizing these array based platforms. The first consistent locus to be discovered was the coagulation factor II (thrombin) receptor-like 3 (F2RL3), by Breitling et al. Breitling et al. used a 27K array to study the effect of smoking on peripheral mononuclear cell pellets and identified several loci that were associated with smoking including F2RL3, GPR15, and ORAI2. The second important locus to emerge was the aryl hydrocarbon receptor repressor (AHRR) uncovered by Monick et al. Monick et al. examined the effect of smoking in lymphoblast and lung macrophage DNA using the Illumina HumanMethylation 450K BeadChip to show that tobacco smoking can cause significant changes in DNA methylation patterns at various genomic loci and especially at AHRR.

A large study carried by Zeilinger et al. further confirmed the changes in DNA methylation patters at the above noted loci and extended the list of genes to include HIVEP3 and CACNA1D. Other genetic loci have also emerged to contain smoking-specific CpG sites including 2q37, 6p21.33, growth factor independent 1 transcription repressor (GFI1), myosin IG (MYO1G), CPOX, GPR15, CYP1A1, and many others.

The DNA methylation signatures of candidate sites have been shown to serve as useful biomarkers for various traits. Interest in such applications has resulted in several genome wide association studies using large scale epigenetic arrays. However, because DNA methylation analysis is mainly performed by array studies which require laborious bioinformatics analysis, applying DNA methylation is still difficult in the clinical and forensic regimes due to the complexity of the instrumentation and the need for relatively large sample quantities.

BRIEF SUMMARY OF THE INVENTION

In certain embodiments, the invention provides methods to identify DNA methylation status at specific CpG sites in a cell. The DNA methylation status at specific CpG sites in a cell can then be used to identify smoking habits of the person from which the cell originated. In specific embodiments, DNA methylation is determined using PCR amplification using specific primers on bisulfite treated genomic DNA isolated from the cell. The PCR amplicons so produced can be sequenced, for example, by pyrosequencing, using specific primers to identify DNA methylation status of the specific CpG sites. Such methods allow the determination of the methylation status with high accuracy and speed. As such, certain embodiments of the invention provide quick and easy methods that can be used to readily determine the DNA methylation status of certain sites for small amounts of samples between about 0.1 to about 500 ng genomic DNA. Also, the methods described herein can be designed in a high-throughput manner to process a large number of samples.

In one embodiment, the status of methylation at specific CpG sites at the AHRR locus in the genomic DNA isolated from a sample is used to determine smoking habits of the person from which the cell originated.

In another embodiment, the methylation status at specific CpG sites at the AHRR locus in the genomic DNA isolated from a person is determined by pyrosequencing using specific primers described herein.

Kits containing primers and reagents for carrying out the methods disclosed herein are also provided.

Further, assays for determining the methylation status at certain CpG sites at the AHRR locus in the genomic DNA isolated from a person are provided. In certain embodiments, the assays comprise pyrosequencing using specific primers described herein.

BRIEF DESCRIPTION OF SEQUENCES

Figure 1:
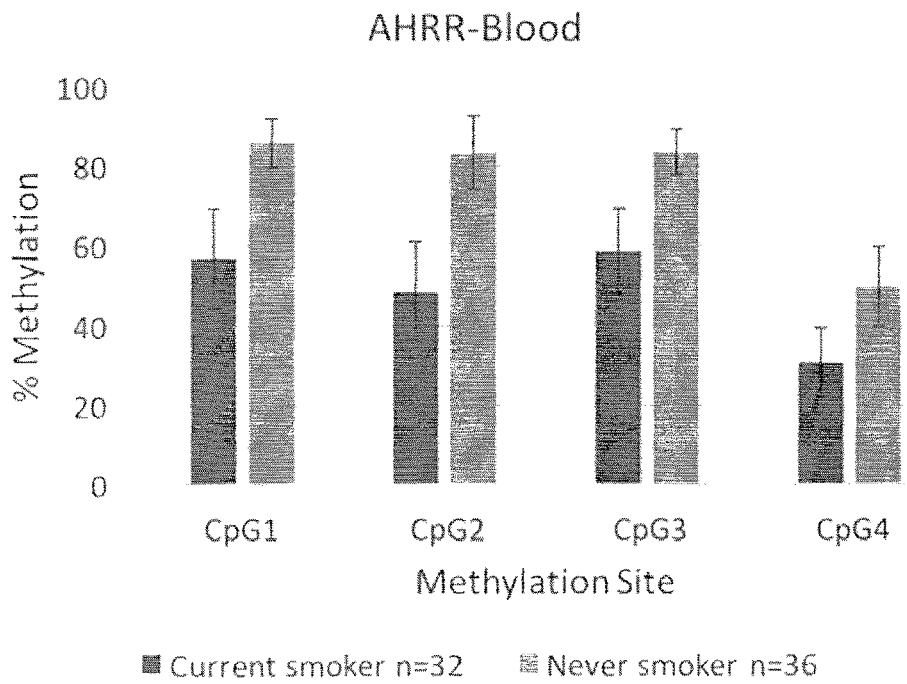
FIG. 1 shows mean percent methylation for certain CpG sites in AHRR gene in blood from current smoker and never smoker groups. Error bars are standard deviation from the mean.

SEQ ID NO: 1: Sequence of the 169 bp amplicon in AHRR locus.
SEQ ID NO: 2: Sequence of a forward primer designed to amplify the AHRR locus.
SEQ ID NO: 3: Sequence of a reverse primer designed to amplify the AHRR locus.
SEQ ID NO: 4: Sequence of a sequencing primer designed to sequence the AHRR locus.
SEQ ID NO: 5: Sequence of 169 bp amplicon in AHRR locus after bisulfite treatment assuming 100% methylation of all CpG sites.
SEQ ID NO: 6: Forward primer of set 1.
SEQ ID NO: 7: Reverse primer of set 1.
SEQ ID NO: 8: Sequencing primer of set 1.
SEQ ID NO: 9: Forward primer of set 2.
SEQ ID NO: 10: Reverse primer of set 2.
SEQ ID NO: 11: Sequencing primer of set 2.
SEQ ID NO: 12: Forward primer of set 3.
SEQ ID NO: 13: Reverse primer of set 3.
SEQ ID NO: 14: Sequencing primer of set 3.
SEQ ID NO: 15: Forward primer of set 4.
SEQ ID NO: 16: Reverse primer of set 4.
SEQ ID NO: 17: Sequencing primer of set 4.
SEQ ID NO: 18: Forward primer of set 5.
SEQ ID NO: 19: Reverse primer of set 5.
SEQ ID NO: 20: Sequencing primer of set 5.
SEQ ID NO: 21: Forward primer of set 6.
SEQ ID NO: 22: Reverse primer of set 6.
SEQ ID NO: 23: Sequencing primer of set 6.
SEQ ID NO: 24: Forward primer of set 7.
SEQ ID NO: 25: Reverse primer of set 7.
SEQ ID NO: 26: Sequencing primer of set 7.
SEQ ID NO: 27: Forward primer of set 8.
SEQ ID NO: 28: Reverse primer of set 8.
SEQ ID NO: 29: Sequencing primer of set 8.
SEQ ID NO: 30: Forward primer of set 9.
SEQ ID NO: 31: Reverse primer of set 9.
SEQ ID NO: 32: Sequencing primer of set 9.
SEQ ID NO: 33: Forward primer of set 10.
SEQ ID NO: 34: Reverse primer of set 10.
SEQ ID NO: 35: Sequencing primer of set 10.
SEQ ID NO: 36: Forward primer of set 11.
SEQ ID NO: 37: Reverse primer of set 11.
SEQ ID NO: 38: Sequencing primer of set 11.
SEQ ID NO: 39: Forward primer of set 12.
SEQ ID NO: 40: Reverse primer of set 12.
SEQ ID NO: 41: Sequencing primer of set 12.
SEQ ID NO: 42: Forward primer of set 13.
SEQ ID NO: 43: Reverse primer of set 13.
SEQ ID NO: 44: Sequencing primer of set 13.
SEQ ID NO: 45: Forward primer of set 14.
SEQ ID NO: 46: Reverse primer of set 14.
SEQ ID NO: 47: Sequencing primer of set 14.
SEQ ID NO: 48: Forward primer of set 15.
SEQ ID NO: 49: Reverse primer of set 15.
SEQ ID NO: 50: Sequencing primer of set 15.
SEQ ID NO: 51: Forward primer of set 16.
SEQ ID NO: 52: Reverse primer of set 16.
SEQ ID NO: 53: Sequencing primer of set 16.
SEQ ID NO: 54: Forward primer of set 17.
SEQ ID NO: 55: Reverse primer of set 17.
SEQ ID NO: 56: Sequencing primer of set 17.
SEQ ID NO: 57: Forward primer of set 18.
SEQ ID NO: 58: Reverse primer of set 18.
SEQ ID NO: 59: Sequencing primer of set 18.
SEQ ID NO: 60: Forward primer of set 19.
SEQ ID NO: 61: Reverse primer of set 19.
SEQ ID NO: 62: Sequencing primer of set 19.
SEQ ID NO: 63: Forward primer of set 20.
SEQ ID NO: 64: Reverse primer of set 20.
SEQ ID NO: 65: Sequencing primer of set 20.
SEQ ID NO: 66: Forward primer of set 21.
SEQ ID NO: 67: Reverse primer of set 21.
SEQ ID NO: 68: Sequencing primer of set 21.

DETAILED DESCRIPTION OF THE INVENTION

Accordingly, certain embodiments of the invention provide methods for identifying a person as a current, former, or never smoker based on DNA methylation status of certain CpG sites in the genomic DNA isolated from the person. The methods of the invention depend on the analysis of methylation status at a specific genetic locus, namely, the AHRR locus, to detect a person's smoking habits. The sample may be, for example, a body fluid. In general, the technology proposed herein is automatable. This technology can be used with trace levels of DNA recovered from crime scenes to serve as intelligence tool in case of unknown DNA profiles. In addition, the technique may also be used in clinical fields for use as a diagnostic marker for certain diseases, such as lung infections. The invention can also be used by insurance companies, for example, health insurance companies, to identify smoking status of an individual.

In particular, the invention provides four main advantages over other conventional methods. First, it utilizes a novel set of CpG sites that can be used to identify a person as a current, former or never smoker based on DNA methylation status. Second, the method is simple and cost effective, as it utilizes only one singleplex PCR reaction and pyrosequencing. Third, the CpG sites tested herein provide the strongest association with tobacco smoking. Fourth, the system was tested against the blood and saliva, which are the two types of body fluids most frequently encountered in crime scene and easily acquired from patients. As such, the invention provides simple, cost effective and the sensitive assays to differentiate current, former and never tobacco smokers as well as to detect any epigenetic modifications that relate to lung-related diseases.

As noted above, a DNA methylation marker discovered to be associated with tobacco smoking is the CpG site (cg05575921, Chr5:373,378) at the AHRR gene. This disclosure provides a new set of CpG sites that provides stronger association with the smoking habits than the CpG site at cg05575921. The new CpG sites provide a greater difference in methylation level between never smokers and current smokers.

Figure 2:
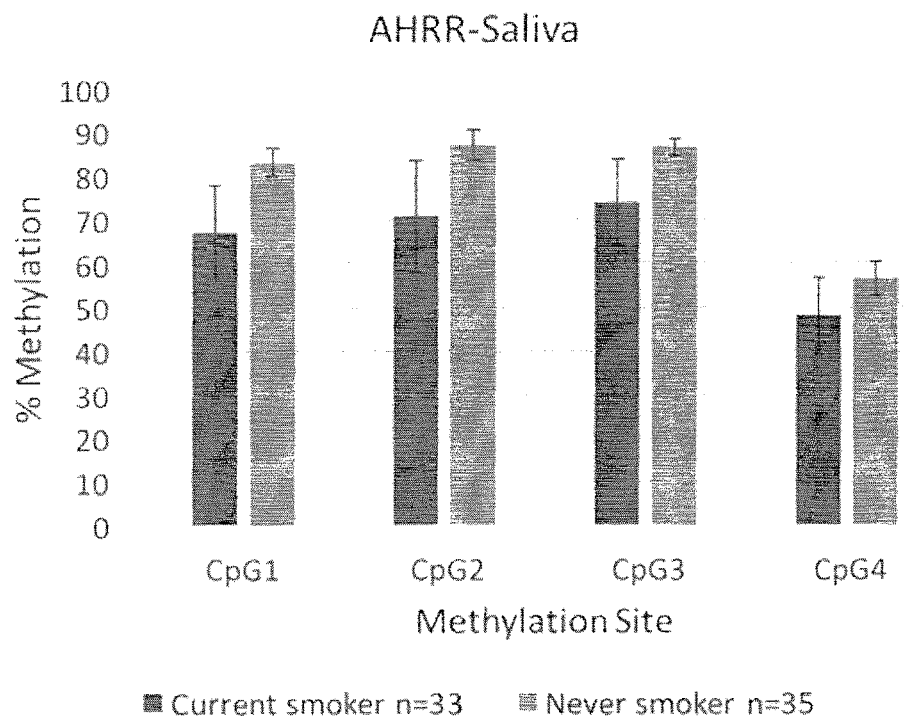
FIG. 2 shows mean percent methylation for certain CpG sites in AHRR gene in saliva from current smoker and never smoker groups. Error bars are standard deviation from the mean.

Accordingly, in certain embodiments, the invention provides a novel set of four CpG sites in the human genome that can be used as an effective marker for tobacco smoking. These four CpG sites are a subset of the top ranked 15 CpG sites in blood and 10 CpG sites in saliva identified using Benjamini-Hochberg method. These methylation sites are located at AHRR gene as follows, CpG1 at Chr5:373,476, CpG2 at Chr5:373,490, CpG3 at Chr5:373,494, and CpG4 at Chr5:373,529 (chromosome location according to worldwide website: genome.ucsc.edu/GRCh37/hg19). In specific embodiments, the invention describes a set of primers for PCR and pyrosequencing that can quantify DNA methylation status of these novel CpG sites at the AHRR gene. The new set of primers (Table 1) were designed to amplify and analyze the genome coordinates chr5: 373,438-373,606 (169 bp product). The region is amplified and analyzed by the primers designed to include the four CpG sites, particularly, the cytosines at positions Chr5:373,476, Chr5:373.490, Chr5:373,494 and Chr5:373,529 of SEQ ID NO: 1. These four CpG sites showed a statistically significant decrease in average methylation status for current smokers when compared to never smokers in blood and saliva as shown in FIGS. 1 and 2. In addition, statistical significance ANOVA and Kruskal-Wallis tests that illustrate the performance of these CpG sites in blood and saliva to differentiate the three smoking groups are shown in Table 3. All the samples were collected from 86 volunteers. The primer sequences are shown in Table 1.

TABLE 1

Assay design and primer sequences targeting 4 CpG sites in AHRR locus for tobacco smoking.

| Locus | | Sequence | Chr./ Gene ID | Amp. size | CpG sites analyzed (bold and underlined) (sequence to analyze) |
|---|---|---|---|---|---|
| AHRR | Forward | GGGAGTGGTTTTGG TAGG (SEQ ID NO: 2) | 5/57491 | 169 | TTGYGGGATTAGTA GGTYGGGYGGTGGT TGGGAGGTAGGGG ATAGGTTGGTTTTT GYGGTTTTGGAGGT ATAGAGTTTTTTT (Underlined residues are located at positions 39, 53, 57, and 92 of SEQ ID NO: 5) |
| | Reverse* | ACCCTTACAAAACA CAACTAAAC (SEQ ID NO: 3) | | | |
| | Sequencing | AGGGTTTTTTTTTGT AGATT (SEQ ID NO: 4) | | | |

Chr.: chromosome
*biotinylated primer
Amp.: Amplicon

Pyrosequencing was used to identify CpG sites indicative of tobacco smoking by investigating DNA sequences surrounding genetic loci AHRR, 2q37.1, 6p21.33, GFI1, F2RL3, and MYO1G (Tables 9 and 10). A set of novel CpG sites associated with tobacco smoking were detected in all six genetic loci. Stickily, in AHRR locus, the blood methylation data revealed that a cluster of 23 consecutive CpG sites (Chr5:373,115, Chr5:373,119, Chr5:373,147, Chr5:373,193, Chr5:373,199, Chr5:373,203, Chr5:373,248, Chr5:373,250, Chr5:373,299, Chr5:373,315, Chr5:373,353, Chr5:373,355, Chr5:373,378, Chr5:373,398, Chr5:373,423, Chr5:373,476, Chr5:373,490, Chr5:373,494, Chr5:373,529, Chr5:373,555, Chr5:373,609, Chr5:373,651, Chr5:373,653) including the two probes sites cg05575921 (Ch5:373,378) and cg23576855 (Ch5:373,299) were significantly hypomethylated in current smokers compared to never smokers. In saliva, a subset of 10 CpGs from the 23 consecutive CpGs mentioned above were also significantly hypomethylated in current smokers compared to never smokers. Particularly, the CpG sites located at Ch5:373,490 for blood and Ch5:373,476 for saliva were significantly hypomethylated in current smokers compared to never smokers with a decrease in mean methylation in current smokers of 42.3% (p-value=$3.39\times10^{-4}$) and 21.3% (p-value=$2.98\times10^{-4}$), respectively (Table 10).

In certain embodiments, a 4-CpG methylation assay is provided that identifies the methylation status of four specific CpG sites in cells obtained from blood or saliva that are most indicative of an individual's smoking habits. For blood, a stepwise multinomial logistic regression model (MLR) combining two CpG sites in the assay was very effective by correctly predicting 90.6% of current smokers, 38.9% of former smokers, and 91.7% of never smokers. In saliva, a combined MLR containing all 4 CpGs correctly predicted 84.8% of current smokers, 64.7% of former smokers and 85.7% of never smokers (Table 8). Certain embodiments of the invention provide assays for the determination of DNA methylation status at certain CpG sites, for example, pyrosequencing-based assays to determine DNA methylation of specific CpG sites, for identifying individuals who smoke tobacco, particularly in genomes obtained from cells in blood or saliva.

In accordance with the subject invention, it has been found that the DNA methylation status at the AHRR locus is different in cells, particularly, in the cells from blood or saliva, obtained from former, current, and never smokers.

Identifying a person as a former, current, or never smoker based on DNA methylation status according to the methods provided herein does not depend on accurate quantification of human DNA present in the sample. Instead, such identification is determined through the use of specific primers for bisulfite-converted DNA, primer specific amplicons are obtained that correspond to the genomic region of interest, namely, the AHRR locus (SEQ ID NO: 1).

Forensic samples commonly contain DNA from other species, either due to exposure to the environment or due to the presence of several bacterial species that are part of the human microbiome. Therefore, a method that uses nucleic acids for body fluid discrimination must be sufficiently specific to withstand the presence of non-human DNA or RNA. The methods described herein using the locus AHRR are specific for primates and do not amplify genomic DNA from other organisms.

Quantification of DNA methylation status measured by pyrosequencing at the AHRR locus can successfully discriminate source of certain cells as a current, former, or never smoker. The methods described herein can be practiced with small amounts of genomic DNA, for example, between 0.1 ng to 50 ng, particularly, between 5 ng to 30 ng, more particularly, at about 5 ng. Further, the invention provides pyrosequencing methods that are specific for humans. Contaminations usually present in biological samples, for example, bacterial DNA, are not detected.

Accordingly, certain embodiments of the invention provide a method for identifying the origin of a cell as a current smoker, former smoker, or never smoker, comprising the steps of:
  (a) determining the methylation status at AHRR locus in:
    i) a genomic DNA isolated from the cell, and
    ii) optionally, a control genomic DNA;
  (b) optionally, obtaining one or more reference values corresponding to the methylation status at AHRR locus; and
  (c) identifying the origin of the cell as current smoker, former smoker, or never smoker based on the methylation status at AHRR locus in the genomic DNA isolated from the cell.

In preferred embodiments, the invention provides methods of identifying the origin of a cell as a current smoker or never smoker based on the methylation status at AHRR locus in the genomic DNA isolated from the cell.

The term "never smoker" as used herein refers to a person that has never regularly smoked tobacco, particularly, cigarettes in his/her life, and at least over the last five year. Such person has also never been consistently exposed to secondary smoke in his/her life.

The term "former smoker" as used herein refers to a person that has not smoked tobacco, particularly, cigarettes for at least past three years, but previously smoked tobacco, particularly, more than 5 cigarettes a day continuously for at least five years.

The term "current smoker" as used herein refers to a person who smokes tobacco, particularly, cigarette, more than 5 times a day continuously for at least the past five years.

Various techniques are known to a person of ordinary skill in the art to determine the methylation status at the AHRR locus in a genomic DNA. Non-limiting examples of such techniques include bisulfite conversion, digestion by restriction enzymes followed by polymerase chain reaction (Combined Bisulfite Restriction Analysis, COBRA), direct sequencing, cloning and sequencing, pyrosequencing, mass spectrometry analysis or probe/microarray based assay. Certain techniques of determining methylation at certain genomic sites are described in Eads et al., Xiong et al., Paul et al., Warnecke el al., Tost et al., and Ehrich et al., the contents of which are herein incorporated in their entirety. Additional techniques for determining the methylation status at a genetic are known to a person of ordinary skill in the art and such techniques are within the purview of the invention.

The AHRR gene is located on chromosome 5 in humans, more specifically in the region between 304,292 and 438,405 nucleotides. Accordingly, the term "AHRR gene" refers to a polynucleotide having the sequence in the region between 304,292 and 438,405 nucleotides on human chromosome 5. The "AHRR locus" refers to the part of the AHRR gene amplified by the primers of SEQ ID NO: 2 and 3. Accordingly, AHRR locus refers to the sequence of SEQ ID NO: 1, with the genome coordinates of Chr5:373,438 to 373,606. The nucleotide coordinates for genetic loci mentioned herein correspond to University of California Santa Cruz genome browser and Assembly hg19.

The control sample used in the methods of the invention can be obtained from one or more of the following: a cell known to be obtained from a current smoker, former smoker, or never smoker. Preferably, such cells can be obtained from blood or saliva.

If the control sample is a cell from a known current smoker, the step of identifying the origin of a cell as a current smoker is based on the methylation status at the AHRR locus in the genomic DNA isolated from the cell being similar to the methylation status at the AHRR locus in the control genomic DNA. On the other hand, the step of identifying the origin of a cell as a never smoker is based on the methylation status at the AHRR locus in the genomic DNA isolated from the cell being different from the methylation status at the AHRR locus in the control genomic DNA.

If the control sample is a cell from a known never smoker, the step of identifying the origin of a cell as a current smoker is based on the methylation status at the AHRR locus in the genomic DNA isolated from the cell being different from the methylation status at the AHRR locus in the control genomic DNA. On the other hand, the step of identifying the origin of a cell as a never smoker is based on the methylation status at the AHRR locus in the genomic DNA isolated from the cell being similar to the methylation status at the AHRR locus in the control genomic DNA.

The reference value corresponding to the methylation status at the AHRR locus can indicate the methylation status at the AHRR locus in a cell obtained from a current smoker, former smoker, or never smoker, preferably, current smoker or never smoker. As such, the reference value corresponding to methylation status at the AHRR locus can indicate the origin of the cell as a current smoker, former smoker, or never smoker, preferably, current smoker or never smoker.

In one embodiment, the step of determining the methylation status at the AHRR locus of a cell comprises pyrosequencing. Pyrosequencing comprises the steps of:
 (a) isolating the genomic DNA from the cell,
 (b) treating the isolated genomic DNA with bisulfite,
 (c) conducting a PCR using the bisulfite treated DNA as a template and a primer pair designed to amplify the AHRR locus, and
 (d) analyzing the PCR amplicons produced in step (c) by pyrosequencing using a sequencing primer designed to sequence the amplicons.

A primer pair can be designed to amplify the AHRR locus based on the sequence of human genomic DNA flanking the AHRR locus, for example, as shown in SEQ ID NOs: 1 and the sequence of human genomic DNA at the AHRR locus and the human genomic DNA flanking the AHRR locus after being treated with bisulfite, as shown in SEQ ID NOs: 5.

In one embodiment, the primer pair designed to amplify the AHRR locus comprises a forward primer comprising SEQ ID NO: 2 and a reverse primer comprising SEQ ID NO: 3. A skilled artisan can design a primer pair other than SEQ ID NOs: 2 and 3 to amplify the AHRR locus based on the sequences of SEQ ID NOs: 1 and 5 and such embodiments are within the purview of the invention.

In another embodiment, the sequencing primer comprises SEQ ID NO: 4. A skilled artisan can design a sequencing primer other than SEQ ID NO: 4 to sequence the AHRR locus based on the sequences of SEQ ID NOs: 1 and 5 and such embodiments are within the purview of the invention. Alternately, a sequence primer can be designed based on an adapter introduced into the amplicon by incorporating the adapter into one of the forward or reverse primers.

An "adapter" as used herein is a sequence of about 10 to 20 nucleotides that can be introduced into an amplicon by incorporating the adapter into the primer used for the amplification of the amplicon. Once an amplicon contains an adapter sequence, a primer designed based on the sequence of the amplicon can be used to sequence the amplicon.

In certain embodiments, the methods described herein to identify the origin of a cell as current, former, or never smoker are practiced on a forensic sample to determine the source of the cell as a current, former, or never smoker.

In certain embodiments, the invention provides a method for determining the methylation status at the AHRR locus in a genomic DNA from a cell, the method comprising the steps of:
 (a) isolating the genomic DNA from the cell,
 (b) treating the genomic DNA with bisulfite,
 (c) conducting a PCR using the bisulfite treated genomic DNA as a template and a primer pair designed to amplify the AHRR locus, and
 (d) analyzing the PCR amplicons produced in step (c) by pyrosequencing using a sequencing primer designed to sequence the amplicons.

The details described above regarding the techniques for determining the methylation status at the AHRR locus in the genomic DNA in a sample; the AHRR locus; the primer pair designed to amplify the AHRR locus; the sequencing primer designed to sequence the amplicon produced from the AHRR locus; and the types of samples are also applicable to the method described herein for determining the methylation status at the AHRR locus in a genetic material from a cell.

A further embodiment of the invention provides a kit comprising:
 (a) a primer pair designed to amplify the AHRR locus in a bisulfite treated human genomic DNA, and
 (b) a sequencing primer designed to sequence an amplicon produced by a PCR conducted by using the primer pair and the bisulfite treated human genomic DNA as a template.

The details described above regarding the sequences of the primer pair designed to amplify the AHRR locus in a bisulfite treated human genetic material and the sequencing primer designed to sequence the amplicons are applicable to the kits described herein.

In further embodiments, the kit comprises one or more reagents, for example, reagents for treating a sample, reagents for isolating cells from the sample, reagents for isolating genetic material from the sample, reagents for bisulfite treating the genetic material, reagents for conducting PCR, and reagents for conducting pyrosequencing.

As used herein, the singular forms "a," "an" and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

As used herein, the term "methylation status" as applied to a genetic locus refers to whether one or more cytosine residues present in a CpG have or do not have a methylation group. The methylation status refers to the percentage of cells in a sample that do or do not have a methylation group on such cytosines. For example, if 50 cells in a pool of 100 cells contain methylated cytosines at a CpG site, the methylation status of the CpG site is 50%.

Materials and Methods

Sample Collection:

Blood and saliva (buccal swab) samples (n=86 and 85, respectively) were collected from volunteers. Whole blood samples were collected on a cotton swab. The persons were categorized into three groups based on their self-reported smoking history: never smokers, former smokers and current smokers as described in Table 2. Participants in the study were mainly males aged from 6-87 years and whose smoking status was determined based on standardized self-administered questionnaires. The category included individuals who smoked a variety of tobacco products, predominately cigarettes and pipes. Table 2 provides a description of the sample types.

TABLE 2

Demographic characteristics of the population tested groups.

| | Never Smoker | Former Smoker | Current Smoker | Total |
|---|---|---|---|---|
| Description | Lifetime never smoke | Abstinent from smoking for the past 3+ year, but used to smoke tobacco ≥5+ times every day | Smoking tobacco ≥5+ times every day continuous for the past 5+ years | |
| Blood samples | n = 36 | n = 18 | n = 32 | n = 86 |
| Saliva samples | n = 35 | n = 17 | n = 33 | n = 85 |
| Ages | 33 (±14) | 54 (±17) | 40 (±15) | |
| Gender | M = 34, F = 2 | M = 18, F = 0 | M = 22, F = 11 | |

Screening Strategies

Two screening steps were performed to test the association with tobacco smoking. Screening steps were executed using a random subset of the entire samples collected (Table 2) consisting of 8-12 and 6-9 per cell type for each set of current and never smokers. This preliminary screening was important to identify the top ranked methylation sites and thus the best candidates to be used as biomarkers for tobacco smoking. The entire sample set (n=86 for blood and n=85 for saliva) consisting of the three smoking groups was used to test the performance of a 4-CpG biomarker assay developed in this study.

DNA Extraction and Bisulfite Conversion

DNA was extracted from blood and saliva samples using an organic extraction method involving proteinase digestion followed by phenol-chloroform-isoamyl alcohol extraction (Fisher Scientific, NJ). A total DNA volume of 50 μL was recovered and quantified using an Alu-based real-time PCR method with a Rotor-Gene 6000 (Corbett Research, Sydney, Australia, now Qiagen Inc., CA). Two-hundred to five hundred nanograms of extracted DNA were bisulfite-modified using the EpiTect® Fast DNA Bisulfite Kit (Qiagen Inc., CA) to convert the unmethylated cytosines to uracil.

Assay Design

Different epigenome association studies have reported various genetic loci in which methylation status were associated with tobacco smoking. Ten CpG sites at six genetic loci were studied. These six genetic loci include AHRR, 2q37.1, 6p21.33, GFI1, F2RL3, and MYO1G. Methylation status at a broad range of CpG sites in each of these genetic loci was studied with special emphasis in the vicinity around cg05575921 probe site at AHRR. Specific sets of PCR primers were designed using PyroMark Assay Design 2.0 software (Qiagen Inc. CA) to amplify the bisulfite modified target region. The designed assays targeted between two to fourteen CpG sites. One of the PCR primers was biotin labeled to produce biotinylated PCR amplicons needed for the pyrosequencing reaction. Tables 9 and 10 show the location of the tested CpG sites in this study. Finally, a primer set was designed that targeted four consecutive CpG sites at AHRR to serve as an assay for detecting tobacco smoking (Table 1).

PCR and Pyrosequencing

PCR was carried out in a singleplex fashion by utilizing the PyroMark® PCR kit (Qiagen Inc., CA) on the GeneAmp® PCR system 9700 (Applied Biosystems, Foster City, Calif.). The PCR was modified to 15 μl reaction volumes based on the total volume specified by the manufacturer's protocol. The pyrosequencing was done using Pyromark Q24 pyrosequencer (Qiagen Inc., CA) as recommended in the manufacturer's instructions. Pyromark® Q24 software was used to calculate the percent methylation for each CpG site. The results were displayed as a pyrogram with the methylation percentage.

Statistical Analysis

The test of normality was performed using a Shapiro-Wilks test. Because non-normal distributions were detected, smoking-dependent differences in median methylation at single CpG sites between two smoking groups (current smokers versus never smokers) in blood and saliva were tested using a nonparametric Mann-Whitney U-test. In the larger sample set, parametric ANOVA test and nonparametric Kruskal-Wallis test were used to compare the differences in mean and median methylation, respectively, between each of the three smoking groups. Box plots were used to demonstrate the distribution of methylation patterns for the CpG sites across the three smoking groups. P-values of <0.05 were considered to be significant. The Benjamini-Hochberg method was used to control false discovery rate at a level of 0.05 when significant CpGs were claimed among many. The receiver operative curve (ROC) analysis was used to test the performance for each CpG predictive models by calculating the area under the curve (AUC) for each genomic locus tested in the assay. Based on combined and stepwise multinomial logistic regression (MLR) analysis, the methylation data for the 4-CpG assay were used to examine the accuracy of each predictive model of tobacco smoking. All the analyses were performed using SPSS statistics software ver. 23.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Screening Areas for Smoking-Specific CPG Sites

The DNA methylation profiles were explored in current and never smokers around ten of the most frequently reported CpG sites in recent epidemiological studies cg05575921 (Chr5:373,378) in AIHRR, cg03636183 (Chr19:17,000,586) in F2RL3, cg09935388 (Chr1:92,947, 588) in GFI1, cg01940273 (Chr2:233,284,935) in 2q37.1, cg25648203 (Chr5: 395,445) in AHRR, cg21161138 (Chr5: 399,361) in AHRR, cg06126421 (Chr6:30,720,081) in 6p21.33, cg21566642 (Chr2:233,284,662) in 2q37.1, cg23576855 (Chr5:373,299) in AHRR and cg12803068 (Chr7:45,002,919) in MVIYO1G). All ten loci were previously found to be differentially methylated upon tobacco smoking in blood. In the first stage of the study, the methylation status of these 10 selected probe sites was examined along with 22 additional novel CpG sites located nearby. From the total samples collected (n=86 for blood and n=85 for saliva), 8-12 participants for each group of current and never smokers were randomly selected to investigate the methylation profiles of the 32 CpGs in blood and saliva.

The results of the mean percent methylation profiles for the current versus never smokers in blood and saliva samples were used to evaluate the association of the initial 32 tested CpGs with tobacco smoking (Table 9). In this initial evaluation step, significant differences in methylated CpG sites (U-test p-value <0.05) could be detected between current and never smokers in 19 CpG sites in blood and 5 CpGs sites in saliva with p-values ranging from $3.48 \times 10^{-4}$ to $4.10 \times 10^{-2}$ and $1.41 \times 10^{-3}$ to $3.73 \times 10^{-2}$ for blood and saliva, respectively. The majority of tested sites exhibited smoking-induced methylation changes when tested using blood (Table 9).

Among all the genomic loci tested at this preliminary step, AHRR gene and in particular the area located around cg05575921 was found to contain the highest number of smoking-specific CpG sites. Therefore, a wider range of CpG sites located around this particular probe site in AHRR was investigated further.

Example 2—Closer Epigenomic Screening Around cg05575921

The second step in this study was to investigate additional CpG sites near the cg05575921 probe in AHRR. This part of the analysis was focused on identifying the most significant differentially methylated CpGs as a result of tobacco smoking in the selected region. 56 CpGs near cg05575921 probe in AHRR were examined by recording the DNA methylation values of current and never smokers in blood and saliva (n=6-12, for each group per cell type). 11 primer sets were designed to screen the methylation status at the selected CpG sites (Table 12). Table 10 shows the results of the mean methylation percentage at the 56 CpG sites for current smokers versus never smokers. From the methylation data obtained by pyrosequencing, a new set of CpG sites was identified showing significant hypomethylation with current smokers in blood and saliva. Combining the results from Tables 9 and 10, a cluster of 23 consecutive CpG sites starting from CpG site at position Chr5:373,115 to CpG site at Chr5:373,653 were identified to be significantly hypomethylated with current smokers in blood (p-value <0.05). In addition, 10 out of the 23 consecutive CpGs were also significantly associated with tobacco smoking in saliva. The Benjamini-Hochberg method at a 0.05 false discovery rate was used to detect and rank the most significant CpGs tested (Table 11). The Benjamini-Hochberg method identified 15 and 10 CpG sites showing significant decrease in methylation status with current smokers in blood and saliva, respectively.

The most striking and significant CpG site identified was at Chr5:373,490 with a decrease in mean methylation of 42.3% (p-value=$3.39 \times 10^{-4}$) in the blood of current smokers. In saliva, the CpG sites at Chr5:373,476 showed the greatest decrease in mean methylation for current smokers equal to 21.3% (p-value=$2.98 \times 10^{-4}$).

Example 3—Biomarker for Tobacco Smoking

Quick and easy assays that could distinguish current, former, and never smokers are provided. The assays are designed based on the top ranked CpG sites identified in the preliminary analyses for blood and saliva. A preferred assay is designed to determine methylation status at one or more of four consecutive CpG sites at AHRR locus. These four CpG sites are located at Chr5:373,476 (CpG1), Chr5:373,490 (CpG2), Chr5:373,494 (CpG3) and Chr5:373,529 (CpG4). Methylation status of these sites was highly specific in smokers versus never smokers (Table 3).

Figure 3:
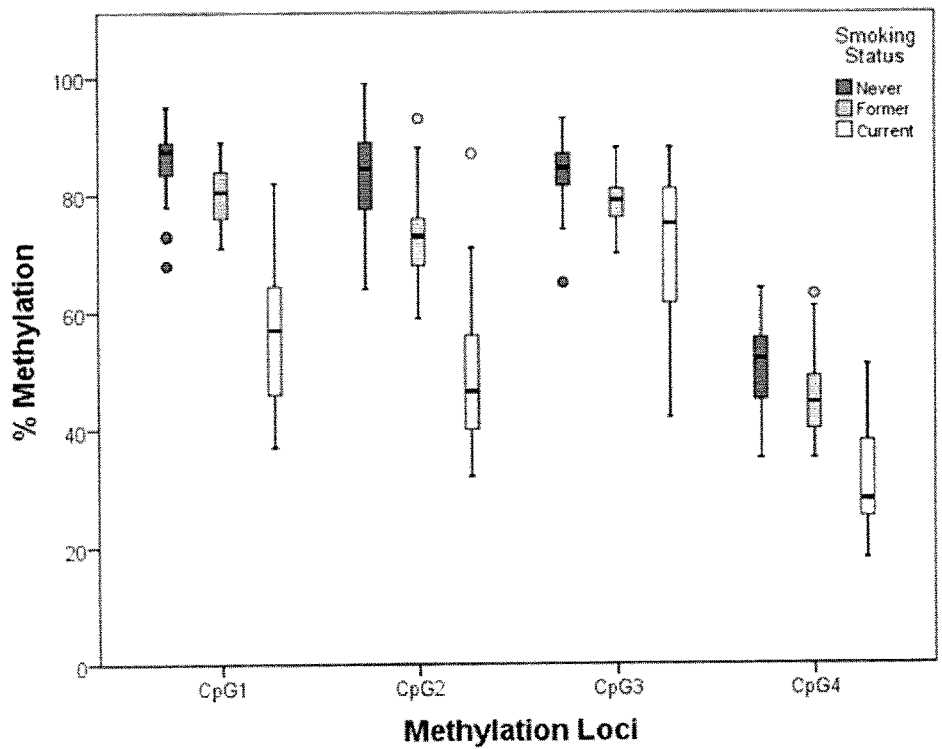
FIG. 3 provides box plots of distribution for methylation at certain CpG sites included in the 4-CpG assay for never, former, and current smokers in blood. The boxes in the plots represent the 25% and 75% percentile, whiskers represent the non-outlier range, dots indicate outliers, and stars show extreme outliers.
Figure 4:
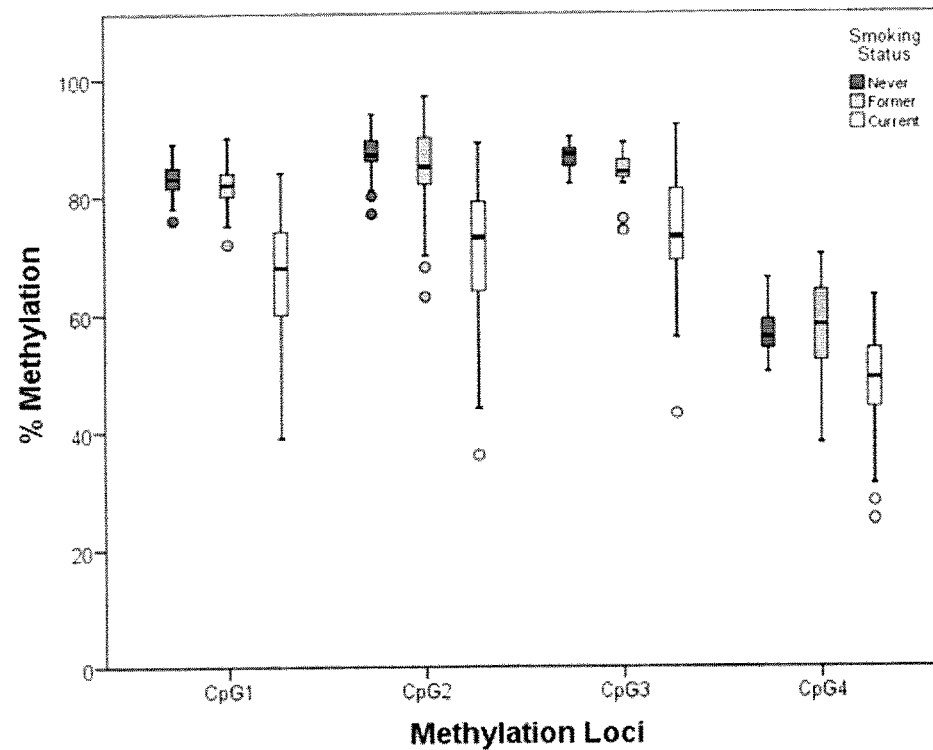
FIG. 4 provides box plots of distribution for methylation at certain CpG sites included in the 4-CpG assay for never, former, and current smokers in saliva. The boxes in the plots represent the 25% and 75% percentile, whiskers represent the non-outlier range, dots indicate outliers, and stars show extreme outliers.

A more preferred assay provides screening methylation profiles utilizing a singleplex bisulfite modified PCR followed by pyrosequencing. One such assay was tested using the collected sample set (n=86 for blood and n=85 for saliva) in which the persons were categorized into three groups based on self-reported smoking history (Table 2). Box plots show the difference in methylation status between never, former, and current smokers for the 4 CpG sites in blood and saliva (FIGS. 3 and 4).

The pronounced association with tobacco smoking at the 4 CpG sites could be confirmed in both the parametric and nonparametric approaches using ANOVA and Kruskal-Wallis tests, and the smoking status could also be distinguished (Table 3).

TABLE 3

Mean methylation % for the 4-CpG sites in the assay and the significance value based on ANOVA (p-value) and Kruskal-Wallis test (P-value).

| Genomic locus | CpG position number | Smoking status (% mean methylation ± standard deviation) for blood | | | | | Smoking status (% mean methylation ± standard deviation) for saliva | | | | |
|---|---|---|---|---|---|---|---|---|---|---|---|
| | | Never n = 36 | Former n = 18 | Current n = 32 | p-value | P-value | Never n = 35 | Former n = 17 | Current n = 33 | p-value | P-value |
| Chr5:373,476 | CpG1 | 85.8 ± 6.1 | 79.9 ± 5.3 | 56.8 ± 12 | $3.2 \times 10^{-22}$ | $2.2 \times 10^{-13}$ | 83.1 ± 3.1 | 81.6 ± 4.9 | 67.2 ± 11 | $6.5 \times 10^{-14}$ | $7.4 \times 10^{-11}$ |
| Chr5:373,490 | CpG2 | 83.4 ± 9.1 | 73.3 ± 8.5 | 48.6 ± 12 | $1.6 \times 10^{-22}$ | $3.9 \times 10^{-13}$ | 87.1 ± 3.4 | 83.7 ± 8.8 | 70.8 ± 13 | $5.5 \times 10^{-10}$ | $2.0 \times 10^{-8}$ |
| Chr5:373,494 | CpG3 | 83.5 ± 5.6 | 78.7 ± 5.1 | 58.7 ± 11 | $1.1 \times 10^{-21}$ | $7.2 \times 10^{-13}$ | 86.4 ± 2.0 | 83.5 ± 4.7 | 73.9 ± 9.9 | $8.6 \times 10^{-11}$ | $8.1 \times 10^{-10}$ |
| Chr5:373,529 | CpG4 | 49.8 ± 9.9 | 45.4 ± 7.7 | 30.8 ± 8.5 | $8.7 \times 10^{-13}$ | $2.1 \times 10^{-10}$ | 56.5 ± 3.8 | 57.2 ± 8.9 | 48.1 ± 8.8 | $5.4 \times 10^{-6}$ | $1.6 \times 10^{-5}$ |

Based on receiver operating characteristic (ROC) analyses, each of the four CpG sites were used in a single CpG assay to determine the best CpG site for discriminating current smokers from former or never smokers. The areas under the curve (AUC) for each CpG site used to discriminate current smokers versus never smoker, current smokers versus former smokers, and never smoker versus former smokers are shown in Tables 4 and 5 for blood and saliva samples, respectively.

TABLE 4

Summary of ROC area under the curve (AUC) analyses for each of the 4 CpG sites in the biomarker assay in blood.

| Genomic locus | CpG position number | Current versus never smokers (in blood) AUC (95% CI) | Current versus former smokers (in blood) AUC (95% CI) | Never versus former smokers (in blood) AUC (95% CI) |
|---|---|---|---|---|
| Chr5:373,476 | CpG1 | 0.983 (0.961-1.00) | 0.947 (0.887-1.00) | 0.786 (0.663-0.909) |
| Chr5:373,490 | CpG2 | 0.975 (0.935-1.00) | 0.947 (0.885-1.00) | 0.795 (0.666-0.924) |
| Chr5:373,494 | CpG3 | 0.977 (0.947-1.00) | 0.944 (0.874-1.00) | 0.753 (0.613-0.893) |
| Chr5:373,529 | CpG4 | 0.932 (0.868-0.997) | 0.892 (0.806-0.979) | 0.694 (0.541-0.848) |

TABLE 5

Summary of ROC area under the curve (AUC) analyses for each of the 4 CpG sites in the biomarker assay in saliva.

| Genomic locus | CpG position number | Current versus never smokers (in saliva) AUC (95% CI) | Current versus former smokers (in saliva) AUC (95% CI) | Never versus former smokers (in saliva) AUC (95% CI) |
|---|---|---|---|---|
| Chr5:373,476 | CpG1 | 0.951 (0.901-1.00) | 0.907 (0.827-0.988) | 0.605 (0.431-0.779) |
| Chr5:373,490 | CpG2 | 0.913 (0.841-0.984) | 0.803 (0.672-0.934) | 0.596 (0.401-0.790) |
| Chr5:373,494 | CpG3 | 0.934 (0.866-1.00) | 0.832 (0.718-0.947) | 0.684 (0.510-0.858) |
| Chr5:373,529 | CpG4 | 0.821 (0.714-0.927) | 0.767 (0.618-0.917) | 0.450 (0.246-0.653) |

The ROC analyses indicate that CpG1, CpG2, and CpG3 individually provide similar discrimination power to distinguish current smokers from former or never smokers in blood with AUC values ranging from 0.983 to 0.944. In addition, CpG1 was determined to be the best indicator in saliva with AUC values ranging from 0.951 to 0.907. Among all CpG sites in the assay, CpG4 gave the lowest AUC values in blood and saliva. Data generated from the ROC analyses demonstrated a lower discrimination power to distinguish former smokers from never smokers in blood and even lower in saliva (Tables 4 and 5). The performance of each of the four CpG sites in the assay were tested by selecting cut off values to separate current, former and never smokers based on the highest sum of specificity and sensitivity (Tables 6 and 7). The accuracies of the individual CpG using ROC analyses were compared with the combined CpG sites accuracies using multinomial logistic regression (MLR) model based on two methods: a combined method using all four CpG sites and a stepwise method using selected CpG sites. The individual ROC analyses and the MLR models gave similar total accuracies of prediction in blood. However, the stepwise MLR model using CpG2 and CpG4 was the best predictor model for current and never smoking status correctly predicting 90.6% of current smokers, 38.9% of former smokers, and 91.7% of never smokers (Table 8). In saliva, the combined MLR method gave the best accuracy overall correctly predicting 84.8% of current smokers, 64.7% of former smokers, and 85.7% of never smokers (Table 8).

TABLE 6

Accuracy of prediction for each of the four CpGs of the assay in blood.

| Genomic locus | CpG position number | Cutoff value for current versus former smoker | Cutoff value for never versus former smoker | Current smoker | Former smoker | Never smoker | Total |
|---|---|---|---|---|---|---|---|
| Chr5:373,476 | CpG1 | 73% | 83.5% | 90.6% | 61.1% | 75% | 77.9% |
| Chr5:373,490 | CpG2 | 63% | 76.5% | 90.6% | 66.7% | 77.8% | 80.2% |
| Chr5:373,494 | CpG3 | 70.5% | 81.5% | 90.6% | 72.2% | 75% | 80.2% |
| Chr5:373,529 | CpG4 | 39.5% | 47% | 81.1% | 50.0% | 66.7% | 68.6% |

TABLE 7

Accuracy of prediction for each of the four CpGs of the assay in saliva.

| Genomic locus | CpG position number | Cutoff value for current versus former smoker | Cutoff value for never versus former smoker | Current smoker | Former smoker | Never smoker | Total |
|---|---|---|---|---|---|---|---|
| Chr5:373,476 | CpG1 | 79.5% | 82.5% | 87.9% | 47.0% | 62.8% | 69.4% |
| Chr5:373,490 | CpG2 | 81.5% | 85.5% | 78.8% | 35.3% | 80% | 70.6% |

TABLE 7-continued

Accuracy of prediction for each of the four CpGs of the assay in saliva.

| Genomic locus | CpG position number | Cutoff value for current versus former smoker | Cutoff value for never versus former smoker | Accuracy of prediction in saliva | | | |
|---|---|---|---|---|---|---|---|
| | | | | Current smoker | Former smoker | Never smoker | Total |
| Chr5:373,494 | CpG3 | 82.5% | 85.5% | 81.8% | 47.0% | 65.7% | 68.2% |
| Chr5:373,529 | CpG4 | 52.5% | 55.5% | 72.7% | 17.6% | 54.3% | 54.1% |

TABLE 8

Multinomial logistic regression (MLR) models for the 4-CpG assay.

| Type of Model | CpG utilized | Accuracy of prediction in blood | | | | CpG utilized | Accuracy of prediction in saliva | | | |
|---|---|---|---|---|---|---|---|---|---|---|
| | | Current smoker | Former smoker | Never smoker | Total | | Current smoker | Former smoker | Never smoker | Total |
| Combined MLR | All 4 CpGs | 90.6% | 38.9% | 86.1% | 77.9% | All 4 CpGs | 84.8% | 64.7% | 85.7% | 81.2% |
| Stepwise MLR | CpG2 + CpG4 | 90.6% | 38.9% | 91.7% | 80.2% | CpG1 + CpG3 + CpG4 | 81.8% | 58.8% | 88.6% | 80.0% |

Example 4—Identifying Optimal CpG Sites and Combination of CpG Sites for as Markers for Tobacco Smoking In this disclosure, a range of methylation sites at six genetic loci including AHRR, 2q37.1 intergenic region, 6p21.33 intergenic region, growth factor independent 1 transcription repressor (GFI1), myosin IG (MYO1G) were examined with special attention to AHRR.

Novel methylation sites associated with tobacco smoking were identified that had not been previously examined using pyrosequencing. The vast majority of the published studies in tobacco smoking were performed using data generated from array platforms investigating specific CpG probe sites covered within chip arrays. A preliminary analysis was performed to examine 10 of the most significantly associated and replicated CpG probe sites related to tobacco smoking on six different genetic loci (Table 9).

TABLE 9

First set of preliminary data showing mean methylation profiles in current versus never smokers for ten of the most frequently reported CpG sites and 22 additional CpG sites in the nearby vicinity. P-value is calculated using Mann-Whitney U-test.

| Locus/ Primer set | Chromosome location (GRCh37)/ (Illumina ID) | CpG position number | Smoking status (mean methylation percentage)/Body fluid | | | | | |
|---|---|---|---|---|---|---|---|---|
| | | | Current/ Blood n = (8-12) | Never/ Blood n = (8-12) | P-value | Current/ Saliva n = (8-12) | Never/ Saliva n = (8-12) | P-value |
| AHRR/ Set 1 | Chr5:373,378 (cg05575921) | CpG1 | 57.7 | 84.2 | 0.000477 | 43.5 | 51.9 | 0.060405 |
| | Chr5:373,398 | CpG2 | 55.8 | 77.6 | 0.000777 | 45.2 | 58.3 | 0.001986 |
| | Chr5:373,423 | CPG3 | 56.1 | 87.2 | 0.000398 | 67.4 | 80 | 0.001413 |
| AHRR/ Set 2 | Chr5:395,445 (cg25648203) | CpG1 | 78.7 | 89.7 | 0.004569 | 85.2 | 89.4 | 0.007540 |
| | Chr5:395,464 | CpG2 | 64.9 | 70.8 | 0.170877 | 75.1 | 81.3 | 0.037348 |
| | Chr5:395,488 | CpG3 | 43.2 | 52.4 | 0.063280 | 50.5 | 67.1 | 0.002745 |
| AHRR/ Set 3 | Chr5:399,361 (cg21161138) | CpG1 | 72.2 | 75.6 | 0.013714 | 45.1 | 42.4 | 0.677356 |
| AHRR/ Set 4 | Chr5:373,299 (cg23576855) | CpG1 | 61 | 86.3 | 0.000735 | 59.4 | 65.9 | 0.116239 |
| | Chr5:373,315 | CpG2 | 59.6 | 88.4 | 0.000520 | 56 | 68.5 | 0.104571 |
| 2q37.1/ Set 5 | Chr2:233,284,950 | CpG1 | 12.4 | 16.8 | 0.010843 | 11.4 | 10 | 0.435542 |
| | Chr2:233,284,935 (cg01940273) | CpG2 | 64.4 | 71.2 | 0.052912 | 49.1 | 46.3 | 0.303086 |
| 2q37.1/ Set 6 | Chr2:233,284,662 (cg21566642) | CpG1 | 50.9 | 63.7 | 0.002468 | 28.2 | 24.7 | 0.269080 |
| | Chr2:233,284,672 | CpG2 | 11.8 | 17.5 | 0.028904 | 7.1 | 6.6 | 0.617813 |
| | Chr2:233,284,675 | CpG3 | 12.2 | 21.5 | 0.000348 | 6 | 6.1 | 0.835531 |
| | Chr2:233,284,691 | CpG4 | 28.1 | 31.5 | 0.061651 | 22.1 | 19 | 0.118861 |
| | Chr2:233,284,693 | CpG5 | 17.4 | 17.5 | 0.475598 | 12.1 | 10 | 0.263966 |
| | Chr2:233,284,703 | CpG6 | 29.7 | 32 | 0.098470 | 20.7 | 18.7 | 0.344980 |

TABLE 9-continued

First set of preliminary data showing mean methylation profiles in current versus never smokers for ten of the most frequently reported CpG sites and 22 additional CpG sites in the nearby vicinity. P-value is calculated using Mann-Whitney U-test.

| Locus/ Primer set | Chromosome location (GRCh37)/ (Illumina ID) | CpG position number | Current/ Blood n = (8-12) | Never/ Blood n = (8-12) | P-value | Current/ Saliva n = (8-12) | Never/ Saliva n = (8-12) | P-value |
|---|---|---|---|---|---|---|---|---|
| 6p21.33/ Set 7 | Chr6:30,720,081 (cg06126421) | CpG1 | 67.5 | 81.2 | 0.025558 | 21.2 | 20.1 | 1 |
| | Chr6:30,720,109 | CpG2 | 32.3 | 23.3 | 0.197158 | 6.1 | 7.4 | 0.542298 |
| GFI1/ Set 8 | Chr1:92,947,559 | CpG1 | 40.6 | 54.4 | 0.040960 | 10 | 8.3 | 0.542606 |
| | Chr1:92,947,567 | CpG2 | 45.3 | 55.7 | 0.054694 | 9.9 | 9.1 | 0.909142 |
| | Chr1:92,947,571 | CpG3 | 47.3 | 54.5 | 0.139895 | 15.7 | 13.9 | 0.403371 |
| | Chr1:92,947,581 | CpG4 | 53.1 | 61.1 | 0.119841 | 19.1 | 16.1 | 0.254865 |
| | Chr1:92,947,586 | CpG5 | 65.2 | 80.4 | 0.007772 | 26.3 | 19.7 | 0.240258 |
| | Chr1:92,947,588 (cg09935388) | CpG6 | 61.4 | 74.9 | 0.002464 | 22.6 | 17.1 | 0.305114 |
| F2RL3/ Set 9 | Chr19:17,000,553 | CpG1 | 74.3 | 89.9 | 0.002787 | 68.1 | 73.3 | 0.785796 |
| | Chr19:17,000,568 | CpG2 | 87.2 | 87.5 | 0.884529 | 82.7 | 84.3 | 0.731783 |
| | Chr19:17,000,586 (cg03636183) | CpG3 | 77.9 | 80.5 | 0.594372 | 66.9 | 70.8 | 0.447808 |
| | Chr19:17,000,597 | CpG4 | 72.7 | 73.6 | 0.884954 | 68.2 | 69.5 | 0.648789 |
| MYO1G/ Set 10 | Chr7:45,002,914 | CpG1 | 74.9 | 65 | 0.008538 | 51.7 | 46.3 | 0.145834 |
| | Chr7:45,002,919 (cg12803068) | CpG2 | 79.6 | 68.1 | 0.026743 | 54.8 | 51.1 | 0.449475 |
| | Chr7:45,002,931 | CpG3 | 62.9 | 53.8 | 0.040605 | 30.4 | 27.4 | 0.523707 |

TABLE 10

Second set of preliminary data showing mean methylation profiles in current versus never smokers for 56 CpG sites in the nearby vicinity of cg05575921 and cg23576855 probe sites. P-value is calculated using Mann-Whitney U-test.

| Locus/ Primer set | Chromosome location (GRCh37)/ (Illumina ID) | CpG position number | Current/ Blood n = 6-9 | Never/ Blood n = 6-9 | P-value | Current/ Saliva n = 6-9 | Never/ Saliva n = 6-9 | P-value |
|---|---|---|---|---|---|---|---|---|
| AHRR/ Set 11 | Chr5:373,115 | CpG1 | 89.3 | 94.3 | 0.003639 | 94.5 | 96 | 0.252135 |
| | Chr5:373,119 | CpG2 | 90.3 | 95.5 | 0.005938 | 92.5 | 95.5 | 0.035064 |
| | Chr5:373,147 | CpG3 | 85 | 90.8 | 0.005938 | 85.7 | 92.2 | 0.004922 |
| AHRR/ Set 12 | Chr5:373,193 | CpG1 | 77.3 | 89.5 | 0.003700 | 82.5 | 87.8 | 0.292834 |
| | Chr5:373,199 | CpG2 | 88.2 | 90.8 | 0.006947 | 91.7 | 93 | 0.093696 |
| | Chr5:373,203 | CpG3 | 77.5 | 87.8 | 0.003639 | 80.2 | 85.2 | 0.075046 |
| | Chr5:373,248 | CpG4 | 60.7 | 71.5 | 0.003823 | 64.7 | 71.7 | 0.009745 |
| | Chr5:373,250 | CpG5 | 64.2 | 75.2 | 0.003885 | 67.5 | 74.2 | 0.004847 |
| AHRR/ Set 13 | Chr5:373,353 | CpG1 | 54.6 | 76 | 0.003135 | 55.5 | 52.2 | 0.935622 |
| | Chr5:373,355 | CpG2 | 47.8 | 69 | 0.004678 | 50.7 | 47.2 | 0.871663 |
| AHRR/ Set 14 | Chr5:373,476 | CpG1 | 50.8 | 87 | 0.000407 | 60.7 | 82 | 0.000298 |
| | Chr5:373,490 | CpG2 | 41.8 | 84.1 | 0.000339 | 63.3 | 87.2 | 0.001933 |
| | Chr5:373,494 | CpG3 | 52.8 | 83.7 | 0.000480 | 69.2 | 85.8 | 0.001382 |
| | Chr5:373,529 | CpG4 | 24.8 | 50.3 | 0.011805 | 44 | 56.7 | 0.014916 |
| | Chr5:373,555 | CpG5 | 40.8 | 69.2 | 0.001249 | 79.8 | 83 | 0.522446 |
| AHRR/ Set 15 | Chr5:373,609 | CpG1 | 15.5 | 20.6 | 0.030210 | 50.5 | 51.4 | 0.635256 |
| | Chr5:373,651 | CpG2 | 27.4 | 48.2 | 0.000771 | 58.8 | 66.1 | 0.635256 |
| | Chr5:373,653 | CpG3 | 20.5 | 37.1 | 0.001112 | 50.6 | 58.8 | 0.343139 |
| AHRR/ Set 16 | Chr5:373,698 | CpG1 | 10 | 10.5 | 0.915927 | 25.5 | 26.1 | 0.915989 |
| | Chr5:373,709 | CpG2 | 9.8 | 11 | 0.358243 | 23.6 | 24.2 | 0.916236 |
| AHRR/ Set 17 | Chr5:373,783 | CpG1 | 2.3 | 1.9 | 0.430556 | 2.8 | 3.3 | 0.332084 |
| | Chr5:373,788 | CpG2 | 2.8 | 3.8 | 0.053291 | 8.9 | 9.3 | 0.915677 |
| | Chr5:373,824 | CpG3 | 6.1 | 8 | 0.015368 | 10.5 | 11.1 | 0.395197 |
| AHRR/ Set 18 | Chr5:373,991 | CpG1 | 4.5 | 7.2 | 0.470753 | 3.2 | 1.5 | 0.045092 |
| | Chr5:373,989 | CpG2 | 4.3 | 6.4 | 0.348434 | 5.8 | 1.2 | 0.004922 |
| | Chr5:373,985 | CpG3 | 7 | 7.6 | 0.942259 | 6 | 6 | 1 |
| | Chr5:373,978 | CpG4 | 4.5 | 7.6 | 0.278631 | 3.2 | 1.8 | 0.035791 |
| | Chr5:373,972 | CpG5 | 5 | 7 | 0.507195 | 1.2 | 1.5 | 0.588919 |
| | Chr5:373,966 | CpG6 | 4.5 | 6.8 | 0.344347 | 0.83 | 1.5 | 0.092674 |
| | Chr5:373,962 | CpG7 | 4 | 6.6 | 0.273862 | 0.83 | 1.5 | 0.339556 |
| | Chr5:373,958 | CpG8 | 6.3 | 6.2 | 1 | 5 | 5.2 | 0.598161 |
| | Chr5:373,949 | CpG9 | 4.2 | 6.4 | 0.088688 | 1.7 | 1.7 | 0.858586 |
| | Chr5:373,931 | CpG10 | 3.5 | 5.4 | 0.342968 | 2.3 | 2 | 0.528336 |

TABLE 10-continued

Second set of preliminary data showing mean methylation profiles in current versus never smokers for 56 CpG sites in the nearby vicinity of cg05575921 and cg23576855 probe sites. P-value is calculated using Mann-Whitney U-test.

| Locus/ Primer set | Chromosome location (GRCh37)/ (Illumina ID) | CpG position number | Current/ Blood n = 6-9 | Never/ Blood n = 6-9 | P-value | Current/ Saliva n = 6-9 | Never/ Saliva n = 6-9 | P-value |
|---|---|---|---|---|---|---|---|---|
| | Chr5:373,929 | CpG11 | 5.3 | 5 | 0.662521 | 3.8 | 4 | 0.669764 |
| | Chr5:373,922 | CpG12 | 3.7 | 4.8 | 0.557806 | 1.3 | 1.2 | 0.4898 |
| | Chr5:373,915 | CpG13 | 3.7 | 6.4 | 0.065438 | 2 | 2 | 0.718646 |
| | Chr5:373,913 | CpG14 | 4.3 | 5.8 | 0.717238 | 0.83 | 0.83 | 1 |
| AHRR/ Set 19 | Chr5:374,011 | CpG1 | 6.2 | 3.5 | 0.463245 | 2.5 | 1.7 | 0.03028 |
| | Chr5:374,013 | CpG2 | 4.2 | 2.8 | 0.415063 | 1.8 | 1.3 | 0.092601 |
| | Chr5:374,018 | CpG3 | 11.5 | 3.2 | 0.018733 | 5.3 | 1.8 | 0.003926 |
| | Chr5:374,021 | CpG4 | 4.3 | 3.5 | 0.86788 | 2.2 | 2.5 | 0.240955 |
| | Chr5:374,024 | CpG5 | 5.3 | 3.3 | 0.284957 | 2.3 | 1.7 | 0.055511 |
| | Chr5:374,027 | CpG6 | 2.7 | 1.5 | 0.672203 | 1 | 0.82 | 0.651748 |
| | Chr5:374,033 | CpG7 | 4.8 | 3.2 | 0.604479 | 2.3 | 1.8 | 0.09169 |
| AHRR/ Set 20 | Chr5:375,020 | CpG1 | 90.3 | 90.7 | 0.80503 | 91.5 | 90.8 | 0.731428 |
| | Chr5:375,024 | CpG2 | 95.7 | 96.8 | 0.515153 | 97.2 | 97 | 0.871208 |
| | Chr5:375,046 | CpG3 | 85.5 | 86.7 | 0.246011 | 82.3 | 80.2 | 0.256429 |
| | Chr5:375,066 | CpG4 | 84.3 | 84.5 | 1 | 84.2 | 82.7 | 0.286728 |
| | Chr5:375,133 | CpG5 | 84.3 | 83.8 | 0.368235 | 80.3 | 77.7 | 0.193029 |
| AHRR/ Set 21 | Chr5:375,562 | CpG1 | 95.2 | 95.7 | 0.557421 | 86.5 | 84.5 | 0.374269 |
| | Chr5:375,564 | CpG2 | 94.3 | 93.2 | 0.063664 | 95.3 | 94.8 | 0.557421 |
| | Chr5:375,580 | CpG3 | 97.5 | 97.5 | 1 | 96 | 94.7 | 0.413366 |
| | Chr5:375,594 | CpG4 | 92.2 | 92.5 | 0.80684 | 92.5 | 91.7 | 0.346201 |
| | Chr5:375,610 | CpG5 | 90.8 | 90.3 | 0.445392 | 86.7 | 84.8 | 0.071929 |
| | Chr5:375,613 | CpG6 | 90 | 89 | 0.243345 | 88.2 | 86.8 | 0.116073 |
| | Chr5:375,621 | CpG7 | 97.5 | 95 | 0.111293 | 97.7 | 94 | 0.225666 |

Novel and useful CpG sites that were hypomethylated in current smokers were detected in the nearby sequences at the majority of the probes tested especially in blood. New clusters of CpG sites associated strongly with tobacco smoking in blood were observed near cg09935388, cg21566642 and cg12803068. In particular, CpG sites in sequences surrounding the cg05575921 probe in AHRR were found to contain the highest number of smoking-specific CpGs cluster. Therefore, CpG sites around this particular probe site were investigated further.

56 CpG sites were selected and evaluated within AHRR locus. Within these 56 CpGs, 20 CpGs in blood and 13 CpGs in saliva were observed to be significantly associated with tobacco smoking (p-values <0.05). Combining the results from Tables 9 and 10, a cluster of 23 CpG sites (Chr5:373, 115-Chr5:373,653, see world-wide-website: genome.ucsc.edu/GRCh37/hg19) including the two probes sites cg05575921 and cg23576855 were identified to have the highest number of top-ranked CpG sites associated with tobacco smoking. According to the Benjamini-Hochberg method, 11 CpGs in blood and 7 CpGs in saliva located within the 23-CpG cluster in AHRR were recognized to be highly smoking specific (Table 11). In addition, within the 23-CpG cluster, the highest number of top-ranked CpG sites were discovered including two CpGs at Ch5:373,490 and Ch5:373,476 which ranked the most significant CpG site in blood and saliva, respectively.

TABLE 11

The top ranked and the significant CpG sites identified based on Benjamini-Hochberg method used to control false discovery rate at a level of 0.05.

| | | In Blood | | In Saliva |
|---|---|---|---|---|
| Rank number | Locus | Chromosome location (GRCh37)/ (Illumina ID) | Locus | Chromosome location (GRCh37)/ (Illumina ID) |
| 1 | AHRR | Chr5:373,490 | AHRR | Chr5:373,476 |
| 2 | 2q37.3 | Chr2:233,284,675 | AHRR | Chr5:373,494 |
| 3 | AHRR | Chr5:373,423 | AHRR | Chr5:373,423 |
| 4 | AHRR | Chr5:373,476 | AHRR | Chr5:373,490 |
| 5 | AHRR | Chr5:373,378 (cg05575921) | AHRR | Chr5:373,398 |
| 6 | AHRR | Chr5:373,494 | AHRR | Chr5:395,488 |
| 7 | AHRR | Chr5:373,315 | AHRR | Chr5:374,018 |
| 8 | AHRR | Chr5:373,299 (cg23576855) | AHRR | Chr5:373,250 |
| 9 | AHRR | Chr5:373,651 | AHRR | Chr5:373.147 |
| 10 | AHRR | Chr5:373,398 | AHRR | Chr5:373,989 |
| 11 | AHRR | Chr5:373,653 | | |
| 12 | AHRR | Chr5:373,555 | | |
| 13 | GFI1 | Chr1:92,947,588 (cg09935388) | | |
| 14 | 2q37.3 | Chr2:233,284,662 (cg21566642) | | |
| 15 | F2RL3 | Chr19:17,000,553 | | |

Quick and easy DNA methylation assays to predict smoking status were also developed. One such assay was arranged to include the two most significant CpG sites for tobacco smoker status that were detected in the preliminary analyses along with two adjacent smoking-specific CpG sites. The assay was designed to determine methylation status of four consecutive CpG sites labeled CpG1 to CpG4 located at Chr5:373,476, Chr5:373,490, Chr5:373,494 and Chr5:373, 529 in AHRR, respectively (Table 3). The assay was tested using bisulfite-modified PCR and pyrosequencing for a large sample set (n=86 for blood and n=85 for salvia) in which the participants were divided according to their self-reported smoking behavior into current, former, or never smokers (Table 2). Based on the methylation data generated, CpG1 and CpG2 of the assay (located at Chr5:373,476 and Chr5: 373,490, respectively) displayed hypomethylated profiles with a significant decrease in percent mean methylation between current smokers and never smokers in blood and saliva (Table 3). Tobacco smoking increased the demethylation of these CpG sites in AHRR. This decrease in methylation is concordant with the results observed from a number of other CpG sites detected at various genetic loci. As shown in FIGS. 3 and 4, current and former smokers had low and intermediate methylation status for all CpG sites respectively, when compared with the data from never smokers. In all four CpGs in the assay, the methylation status were significantly lower in current smokers than in never smokers and smaller differences were found between former smokers and never smokers in blood and saliva.

Data generated from using this 4-CpG assay was next examined to determine whether a single CpG or combination of some or all CpGs was optimal for distinguishing smoking status.

Based on ROC analyses, CpG1, CpG2 and CpG3 had high performance in distinguishing current smokers from former or never smokers in blood samples (AUC values=0.983-0.944), whereas CpG4 had lower discrimination power (AUC values=0.892-0.932). In saliva, CpG1 provided the highest AUC with values ranging from 0.951 to 0.907 (Tables 4-5). Thus, this assay performed better in blood DNA than in saliva, which also can be seen when comparing the accuracy values among the CpG sites in blood and saliva (Tables 6-7). Finally, the accuracy of the individual CpG and various combinations of the four CpGs were tested. Overall, the stepwise MLR model containing CpG2 and CpG4 proved to be the best indicator for current and never smokers' status in blood (Table 8). This stepwise MLR model used an iterative process in order to select one or more CpGs based on the four CpGs that would provide optimal discrimination power. In saliva, the combined MLR method considerably improved the prediction accuracies over that obtained through individual ROC analyses. The combined MLR model could correctly predict 81.2% of the total samples tested whereas the best single CpG predictor gave total accuracy of 70.6% using CpG2 (Table 8).

Several studies have shown a correlation between time since quitting smoking, with methylation status eventually reverting to those of never smokers. This trend of methylation profiles seen in former smokers was observed in genetic loci such as F2RL3 locus. In other genes such as AHRR, the methylation status increases on cessation of smoking but never reverts to the level observed in never smokers. The results for the AHRR loci also produced an intermediate mean methylation status for former smokers (FIGS. 3 and 4). Moreover, in concordance with other studies, the methylation status in former smokers at these 4 CpG sites regenerated and returned to the levels close to that of never smokers with increasing time from cessation. Therefore, the AUC values utilized to distinguish former smokers from never smokers using the 4-CpG assay were lower in discriminating power.

The assays described herein eliminated any concern due to potential confounding effects of age and gender in the methylation data. Although the participants in these assays may have significant differences in mean age between smoking groups, the effect of age on methylation status at the four CpGs becomes insignificant in blood and saliva (p-value range=0.180-0.955) when controlled by smoking status. The effect of gender in the methylation pattern at the four CpG sites was also insignificant in blood and saliva (p-value range=0.271-0.940) with one exception at CpG4 due to an extremely low methylation status for one female sample which was considered an extreme outlier (FIG. 3). When excluding this outlier at CpG4 in blood from the methylation data, the gender effect at this locus was also insignificant when controlled by smoking status. This means that the difference in mean methylation of these CpGs is directly due to smoking status not age or gender. Multiple studies have also confirmed that age and gender have no effect in DNA methylation at various CpG sites in AHRR and other loci.

As such, this disclosure provides novel smoking-specific CpG sites in different genes with special emphasis on 23 CpGs cluster located in AHRR showing strong association with tobacco smoking. Overall, using Benjamini-Hochberg method, 15 CpGs in blood and 10 CpGs in saliva showed significant decrease in methylation status with current smokers. A quick and inexpensive biomarker assay consisting of 4 novel CpG sites at AHRR was developed and determined to be a sensitive and specific predictor of smoking behavior using bisulfite conversion followed by pyrosequencing.

TABLE 12

21 primer sets used to target the all 88 CpG sites investigated in this study.

| Locus | Set # | | Sequence | SEQ ID NO: |
|---|---|---|---|---|
| AHRR | Set 1 | Forward | AGGGGTTGTTTAGGTTATAGAT | 6 |
| | | Reverse* | AACCCTACCAAAACCACTC | 7 |
| | | Sequencing | GGTTTTGGTTTTGTTTTGTA | 8 |
| AHRR | Set 2 | Forward | ATAGAGGGGGTTTGGGAGATA | 9 |
| | | Reverse* | AAATTCCCCTACTCTAAACTAATAAATCAA | 10 |
| | | Sequencing | GTGGTGGGATGTAGTTA | 11 |
| AHRR | Set 3 | Forward* | GGGTTGGTGGTGTAGGATATA | 12 |
| | | Reverse | AACCCATCCTACCCAAATCCTAATAATTAA | 13 |
| | | Sequencing | ATAATTAAAAAACCACCCCTA | 14 |
| AHRR | Set 4 | Forward | GTTGGTAGAGTGTTGGTAGGATATA | 15 |
| | | Reverse* | CCTCCAAAACCCCAAAAACCAACCTATC | 16 |
| | | Sequencing | GGGGTTGTTTAGGTTA | 17 |
| 2q37.1 | Set 5 | Forward* | TTTATGGGAAGGGGGAGG | 18 |
| | | Reverse | CCCCACCCCACTTAACCTT | 19 |
| | | Sequencing | CCCACTTAACCTTAACT | 20 |

TABLE 12-continued 21 primer sets used to target the all 88 CpG sites investigated in this study.

| Locus | Set # | | Sequence | SEQ ID NO: |
|---|---|---|---|---|
| 2q37.1 | Set 6 | Forward | ATGGTTTAGGGGGGTTAAAGT | 21 |
| | | Reverse* | CAACCCCTCCCCCTTCCCAT | 22 |
| | | Sequencing | AGTAGAGTTAGGTTTAGGA | 23 |
| 6p21.33 | Set 7 | Forward | TTGGAGAATTTGATGGAGATTGAAGTTAA | 24 |
| | | Reverse* | ACTATCCCTCCCAACCTTA | 25 |
| | | Sequencing | TTTTTTTGAAATTTTATGATTTAGT | 26 |
| GFI1 | Set 8 | Forward | TTTAGTTTAGGTTGGTTATTTTAGTGAG | 27 |
| | | Reverse* | CACCCCTCCCACAATCAATAAATTAACTT | 28 |
| | | Sequencing | ATTTTAGTGAGAGGTTGTAT | 29 |
| F2RL3 | Set 9 | Forward | GTTTTTGGGTTGGGTGTTTATTAG | 30 |
| | | Reverse* | CCAACAACAACACTAAACCATACATAT | 31 |
| | | Sequencing | GTTTTGGTGGTGGGG | 32 |
| MYO1G | Set 10 | Forward | TTTAGGGGTTTTGTTGATAGGGGGAAG | 33 |
| | | Reverse* | ACCTCTAAATCTCCCACAATTTCA | 34 |
| | | Sequencing | ATAGGGGGAAGTTTG | 35 |
| AHRR | Set 11 | Forward | TGAAGAAATAGAGGGTTTTTAGTAGGA | 36 |
| | | Reverse* | TTCACTACAACCAAAAAAAAACTCATTTA | 37 |
| | | Sequencing | TTTGTTGTGGGTATAGG | 38 |
| AHRR | Set 12 | Forward | AATGAGTTTTTTTTGGTTGTAGTGAAT | 39 |
| | | Reverse* | CCCCTATATCCTACCAACACT | 40 |
| | | Sequencing | TTTTTTGGTTGTAGTGAATT | 41 |
| AHRR | Set 13 | Forward | GTGGGGATTGTTTATTTTTGAGAG | 42 |
| | | Reverse* | AACCTATCCCCTACCTCC | 43 |
| | | Sequencing | ATTGTTTATTTTTGAGAGGGTA | 44 |
| AHRR | Set 14 | Forward | GTTTTGGGAGTGGTTTTGGTAG | 45 |
| | | Reverse* | CCCAACCACCCCAATTACCCATAATAAA | 46 |
| | | Sequencing | GTAGGGTTTTTTTTGTAGA | 47 |
| AHRR | Set 15 | Forward | TTGTTGGTTTAGTTGTGTTTTGTAAG | 48 |
| | | Reverse* | CCCAACCACCCCAATTACCCATAATAAA | 49 |
| | | Sequencing | GTTGTGTTTTGTAAGGG | 50 |
| AHRR | Set 16 | Forward | TGTTGGTTTAGTTGTGTTTTGTAAG | 51 |
| | | Reverse* | CAACCCCAATCTCCTCCT | 52 |
| | | Sequencing | TTTATTTATTTATTATGGGTAATTG | 53 |
| AHRR | Set 17 | Forward | AGGAGATTGGGGTTGGAGA | 54 |
| | | Reverse* | ACCACCACCTCCCCAAATCC | 55 |
| | | Sequencing | GGATGGGGGTTTTTT | 56 |
| AHRR | Set 18 | Forward* | AGATTGGGGTTGGAGAGG | 57 |
| | | Reverse | CCCACTTCCCCCCTACTT | 58 |
| | | Sequencing | AAACCAACCAAACCT | 59 |
| AHRR | Set 19 | Forward | GGAGATTGGGGTTGGAGA | 60 |
| | | Reverse* | CCCACTTCCCCCCTACTT | 61 |
| | | Sequencing | AGGTTTGGTTGGTTTTA | 62 |
| AHRR | Set 20 | Forward | TGGTTTGATGGGGAGTAGGTTAA | 63 |
| | | Reverse* | TCCACCTACTAATCAAAATAATTCACACTT | 64 |
| | | Sequencing | TGGGGAGTAGGTTAAT | 65 |
| AHRR | Set 21 | Forward | GGTTTAGTGGGGAGTGAGG | 66 |
| | | Reverse* | TATCCCCTCAAACAAATACTACCTTACCAC | 67 |
| | | Sequencing | AGGGTTGTGTTTTTTTAAT | 68 |

*biotinylated primer

REFERENCES

1. Bird A. DNA methylation patterns and epigenetic memory. Genes Dev 2002; 16:6-21.
2. Fraga M F, Ballestar E, Paz M F, Ropero S, Setien F, Ballestar M L, Heine-Suner D, Cigudosa J C, Urioste M, Benitez J, Boix-Chornet M, Sanchez-Aguilera A, Ling C, Carlsson E, Poulsen P, Vaag A, Stephan Z, Spector T D, Wu Y Z, Plass C, Esteller M. Epigenetic differences arise during the lifetime of monozygotic twins. Proc Natl Acad Sci USA 2005; 102:10604-10609.
3. Martin G M. Epigenetic drift in aging identical twins. Proc Natl Acad Sci USA 2005; 102:10413-10414.
4. Breitling L P, Yang R, Korn B, Burwinkel B, Brenner H. Tobacco-smoking-related differential DNA methylation: 27K discovery and replication. The American Journal of Human Genetics 2011; 88:450-457.
5. Lee K W, Pausova Z. Cigarette smoking and DNA methylation. Front Genet 2013; 4:132.
6. Cuozzo C, Porcellini A, Angrisano T, Morano A, Lee B, Di Pardo A, Messina S, Iuliano R, Fusco A, Santillo M R. DNA damage, homology-directed repair, and DNA methylation. PLoS genetics 2007; 3:e110.
7. Lee E W, D'Alonzo G E. Cigarette smoking, nicotine addiction, and its pharmacologic treatment. Arch Intern Med 1993; 153:34-48.
8. Satta R, Maloku E, Zhubi A, Pibiri F, Hajos M, Costa E, Guidotti A. Nicotine decreases DNA methyltransferase 1 expression and glutamic acid decarboxylase 67 promoter methylation in GABAergic interneurons. Proc Natl Acad Sci USA 2008; 105:16356-16361.
9. Kadonaga J T, Carner K R, Masiarz F R, Tjian R. Isolation of cDNA encoding transcription factor Sp1 and functional analysis of the DNA binding domain. Cell 1987; 51:1079-1090.
10. Ian L, Lin I G, Hsieh C L. Protein binding protects sites on stable episomes and in the chromosome from de novo methylation. Mol Cell Biol 2001; 21:3416-3424.

11. Liu Q, Liu L. Zhao Y, Zhang J, Wang D, Chen J, He Y, Wu J, Zhang Z, Liu Z. Hypoxia induces genomic DNA demethylation through the activation of HIF-1alpha and transcriptional upregulation of MAT2A in hepatoma cells. Mol Cancer Ther 2011; 10:1113-1123.
12. Monick M M, Beach S R, Plume J, Sears R, Gerrard M, Brody G H, Philibert R A. Coordinated changes in AHRR methylation in lymphoblasts and pulmonary macrophages from smokers. American Journal of Medical Genetics Part B: Neuropsychiatric Genetics 2012; 159:141-151.
13. Zeilinger S, Kühnel B, Klopp N, Baurecht H, Kleinschmidt A, Gieger C, Weidinger S, Lattka E, Adamski J, Peters A. Tobacco smoking leads to extensive genome-wide changes in DNA methylation. PloS one 2013; 8:e63812.
14. Shenker N S, Polidoro S, van Veldhoven K, Sacerdote C, Ricceri F, Birrell M A, Belvisi M G, Brown R, Vineis P, Flanagan J M. Epigenome-wide association study in the European prospective investigation into cancer and nutrition (EPIC-turin) identifies novel genetic loci associated with smoking. Hum Mol Genet 2012; 22:843-851.
15. Joubert B R, Haberg S E, Nilsen R M, Wang X, Vollset S E, Murphy S K, Huang Z, Hoyo C, Midttun O, Cupul-Uicab L A, Ueland P M, Wu M C, Nystad W, Bell D A, Peddada S D, London S J. 450K epigenome-wide scan identifies differential DNA methylation in newborns related to maternal smoking during pregnancy. Environ Health Perspect 2012; 120:1425-1431.
16. Dogan M V, Shields B, Cutrona C, Gao L, Gibbons F X, Simons R, Monick M, Brody G H, Tan K, Beach S R. The effect of smoking on DNA methylation of peripheral blood mononuclear cells from African American women. BMC Genomics 2014; 15:151.
17. Bauer M, Fink B, Thürmann L, Eszlinger M, Herberth G, Lehmann I. Tobacco smoking differently influences cell types of the innate and adaptive immune system-indications from CpG site methylation. Clinical epigenetics 2016; 8:83.
18. Zhang Y, Elgizouli M, Schöttker B, Holleczek B, Nieters A, Brenner H. Smoking-associated DNA methylation markers predict lung cancer incidence. Clinical epigenetics 2016; 8:127.
19. Nyren P, Pettersson B, Uhlén M. Solid phase DNA minisequencing by an enzymatic luminometric inorganic pyrophosphate detection assay. Anal Biochem 1993; 208: 171-175.
20. Andersen A M, Dogan M V, Beach S R, Philibert R A. Current and future prospects for epigenetic biomarkers of substance use disorders. Genes 2015; 6:991-1022.
21. Evans B R, Karchner S I, Allan L L, Pollenz R S, Tanguay R L, Jenny M J, Sherr D H, Hahn M E. Repression of aryl hydrocarbon receptor (AHR) signaling by AHR repressor: Role of DNA binding and competition for AHR nuclear translocator. Mol Pharmacol 2008; 73:387-398.
22. Philibert R, Hollenbeck N, Andersen E, Osborn T, Gerrard M, Gibbons F X, Wang K. A quantitative epigenetic approach for the assessment of cigarette consumption. Front Psychol 2015; 6:656.
23. Madi T, Balamurugan K, Bombardi R, Duncan G, McCord B. The determination of tissue-specific DNA methylation patterns in forensic biofluids using bisulfite modification and pyrosequencing. Electrophoresis 2012; 33:1736-1745.
24. Soares Bispo Santos Silva, Deborah, Antunes J, Balamurugan K, Duncan G, Sampaio Alho C, McCord B. Evaluation of DNA methylation markers and their potential to predict human aging. Electrophoresis 2015; 36:1775-1780.
25. Alghanim H, Antunes J, Silva, Deborah Soares Bispo Santos, Alho C S, Balamurugan K, McCord B. Detection and evaluation of DNA methylation markers found at SCGN and KLF14 loci to estimate human age. Forensic Science International: Genetics 2017; 31:81-88.
26. Wan E S, Qiu W, Baccarelli A, Carey V J, Bacherman H, Rennard S I, Agusti A, Anderson W, Lomas D A, DeMeo D L. Cigarette smoking behaviors and time since quitting are associated with differential DNA methylation across the human genome. Hum Mol Genet 2012; 21:3073-3082.
27. Bosse Y, Postma D S, Sin D D, Lamontagne M, Couture C, Gaudreault N, Joubert P, Wong V, Elliott M, van den Berge M, Brandsma C A, Tribouley C, Malkov V, Tsou J A, Opiteck G J, Hogg J C, Sandford A J, Timens W, Pare P D, Laviolette M. Molecular signature of smoking in human lung tissues. Cancer Res 2012; 72:3753-3763.
28. Shenker N S, Ueland P M, Polidoro S, van Veldhoven K, Ricceri F, Brown R, Flanagan J M, Vineis P. DNA methylation as a long-term biomarker of exposure to tobacco smoke. Epidemiology 2013; 24:712-716.
29. Tsaprouni L G, Yang T, Bell J, Dick K J, Kanoni S, Nisbet J, Vifuela A, Grundberg E, Nelson C P, Meduri E. Cigarette smoking reduces DNA methylation levels at multiple genomic loci but the effect is partially reversible upon cessation. Epigenetics 2014; 9:1382-1396.
30. Elliott H R, Tillin T, McArdle W L, Ho K, Duggirala A, Frayling T M, Smith G D, Hughes A D, Chaturvedi N, Relton C L. Differences in smoking associated DNA methylation patterns in south asians and europeans. Clinical epigenetics 2014; 6:4.
31. Endo K, Li J. Nakanishi M, Asada T, Ikesue M, Goto Y, Fukushima Y, Iwai N. Establishment of the MethyLight assay for assessing aging, cigarette smoking, and alcohol consumption. BioMed research international 2015; 2015.
32. Comey C T, Koons B W, Presley K W, Smerick J B, Sobieralski C A, Stanley D M, Baechtel F. DNA extraction strategies for amplified fragment length polymorphism analysis. Journal of Forensic Science 1994; 39:1254-1269.
33. Nicklas J A, Buel E. Development of an alu-based, real-time PCR method for quantitation of human DNA in forensic samples. J Forensic Sci 2003; 48:936-944.
34. Benjamini Y, Hochberg Y. Controlling the false discovery rate: A practical and powerful approach to multiple testing. Journal of the royal statistical society. Series B (Methodological) 1995:289-300.
35. Eads C, Laird P. Combined bisulfite restriction analysis (COBRA). Methods Mol Biol. 2002; 200:71-85.
36. Xiong Z, Laird P. COBRA: a sensitive and quantitative DNA methylation assay. Nucleic Acids Res. 1997; 25:2532-4.
37. Paul C, Clark S. Cytosine methylation: quantitation by automated genomic sequencing and GENESCAN analysis. Biotechniques. 1996; 21:126-33.
38. Warnecke P, Stirzaker C, Song J, Grunau C, Melki J, Clark S. Identification and resolution of artifacts in bisulfite sequencing. Methods. 2002; 27:101-7.
39. Tost J, Gut I. Analysis of gene-specific DNA methylation patterns by pyrosequencing technology. Methods Mol Biol. 2007; 373:89-102.
40. Ehrich M, Nelson M, Stanssens P, Zabeau M, Liloglou T, Xinarianos G, et al. Quantitative high-throughput analysis of DNA methylation patterns by base-specific cleavage and mass spectrometry. Proc Natl Acad Sci USA. 2005; 102:15785-90.

We claim:

1. A kit comprising:
   (a) a primer pair that amplifies in a polymerase chain reaction (PCR) a DNA sequence consisting of SEQ ID NO: 5, and optionally,
   (b) a sequencing primer that sequences in a sequencing reaction an amplicon produced by a PCR conducted by using the primer pair that amplifies the DNA sequence consisting of SEQ ID NO: 5,
   wherein each primer of the primer pair and, when present, the sequencing primer, has a sequence complementary to the sequence of SEQ ID NO: 5 and has between 16 and 30 nucleotides.

2. The kit of claim 1, wherein the primer pair comprises a forward primer comprising SEQ ID NO: 2 and a reverse primer comprising SEQ ID NO: 3.

3. The kit of claim 2, further comprising the sequencing primer comprising SEQ ID NO: 4.

4. The kit of claim 1, the kit comprising the primer pair and the sequencing primer, and wherein the sequencing primer comprises SEQ ID NO: 4.

5. The kit of claim 1, wherein the kit consists of the primer pair.

6. The kit of claim 5, wherein the primer pair consists of: a forward primer comprising SEQ ID NO: 2 and a reverse primer comprising SEQ ID NO: 3.

7. The kit of claim 1, wherein the kit consists of the primer pair and the sequencing primer.

8. The kit of claim 7, wherein the primer pair consists of: a forward primer comprising SEQ ID NO: 2 and a reverse primer comprising SEQ ID NO: 3; and the sequencing primer comprises SEQ ID NO: 4.

9. A method for identifying the origin of a cell as a current smoker, former smoker, or never smoker, comprising the steps of:

(a) determining the methylation status at an AHRR locus of SEQ ID NO: 1 in:
   i) a genomic DNA of the cell, and
   ii) optionally, a control genomic DNA;
   said determining the methylation status at the AHRR locus comprising the steps of:
   A) isolating the genomic DNA from the cell,
   B) treating the isolated genomic DNA with bisulfite,
   C) amplifying in a polymerase chain reaction (PCR) the genomic DNA isolated from the cell and when present, the control genomic DNA, using a primer pair that amplifies the DNA sequence consisting of SEQ ID NO: 5, and,
   D) sequencing the PCR amplicons produced from the genomic DNA isolated from the cell and when present, the control genomic DNA, using a sequencing primer that sequences in a sequencing reaction the DNA sequence consisting of SEQ ID NO: 5,
   wherein each primer of the primer pair and the sequencing primer has a sequence complementary to the sequence of SEQ ID NO: 5 and has between 16 and 30 nucleotides;
(b) optionally, obtaining one or more reference values corresponding to the methylation status at the AHRR locus; and
(c) identifying the origin of the cell as current smoker, former smoker, or never smoker based on the methylation status at the AHRR locus in the genomic DNA isolated from the cell.

10. The method of claim 9, comprising sequencing the PCR amplicons produced from the genomic DNA isolated from the cell and when present, the control genomic DNA, by pyrosequencing the PCR amplicons using the sequencing primer having the sequence complementary to the sequence of SEQ ID NO: 5 and having between 16 and 30 nucleotides.

11. The method of claim 9, wherein the primer pair comprises a forward primer comprising SEQ ID NO: 2 and a reverse primer comprising SEQ ID NO: 3.

12. The method of claim 9, wherein the sequencing primer comprises SEQ ID NO: 4.

13. The method of claim 9, wherein the control sample is a cell known to be obtained from blood or saliva from a current smoker, former smoker, or never smoker.

14. The method of claim 9, comprising identifying the origin of the cell as current smoker or never smoker based on the methylation status at the AHRR locus in the genomic DNA of the cell.

15. The method of claim 9, wherein the cell is obtained from a forensic sample.

16. The method of claim 15, wherein the forensic sample is processed to separate a cell from blood or saliva.

17. A method for determining the methylation status at an AHRR locus of SEQ ID NO: 1 in a genomic DNA of a cell, the method comprising the steps of:
  (a) isolating the genomic DNA from the cell,
  (b) treating the genomic DNA with bisulfite,
  (c) amplifying in a polymerase chain reaction (PCR) the genomic DNA isolated from the cell using a primer pair that amplifies the DNA sequence consisting of SEQ ID NO: 5, and,
  (d) sequencing the PCR amplicons produced from the genomic DNA isolated from the cell using a sequencing primer that sequences in a sequencing reaction the DNA sequence consisting of SEQ ID NO: 5,
  wherein each primer of the primer pair and the sequencing primer has a sequence complementary to the sequence of SEQ ID NO: 5 and has between 16 and 30 nucleotides.

18. The method of claim 17, wherein the primer pair comprises a forward primer comprising SEQ ID NO: 2 and a reverse primer comprising SEQ ID NO: 3.

19. The method of claim 17, wherein the sequencing primer comprises SEQ ID NO: 4.

20. The method of claim 17, comprising sequencing the PCR amplicons produced from the genomic DNA isolated from the cell by pyrosequencing the PCR amplicons using the sequencing primer having the sequence complementary to the sequence of SEQ ID NO: 5 and having between 16 and 30 nucleotides.

21. The method of claim 17, wherein the cell is isolated from a forensic sample.

22. The method of claim 21, wherein the forensic sample is processed to separate a cell from blood or saliva.

* * * * *

SEQUENCE LISTING

<160> NUMBER OF SEQ ID NOS: 68

<210> SEQ ID NO 1
<211> LENGTH: 169
<212> TYPE: DNA
<213> ORGANISM: Homo sapiens

<400> SEQUENCE: 1
gggagtggtc ctggcagggc ccctctctgc agaccctgcg ggaccagcag gccgggcggt     60
ggctgggagg caggggacag gttggcctct gcggtcttgg aggcacagag ctcctcccgc    120
cctgggcctg tggccccctc ctgctggccc agctgtgcct tgtaagggc                169

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
gggagtggtt ttggtagg                                                   18

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
acccttacaa aacacaacta aac                                             23

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agggtttttt tttgtagatt                                                 20

<210> SEQ ID NO 5
<211> LENGTH: 169
<212> TYPE: DNA
<213> ORGANISM: Artificial Sequence
<220> FEATURE:
<223> OTHER INFORMATION: 100% methylated AHRR locus after bisulfite
      treatment

<400> SEQUENCE: 5
gggagtggtt ttggtagggt ttttttttgt agatttgcg ggattagtag gtcgggcggt      60
ggttgggagg taggggatag gttggttttt gcggttttgg aggtatagag ttttttttcgt   120 tttgggtttg tggttttttt ttgttggttt agttgtgttt tgtaagggt                169

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6 agggggttgtt taggttatag at                                              22

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
aaccctacca aaaccactc                                                   19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggttttggtt ttgttttgta                                                  20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9 atagagggggg tttgggagat a                                               21

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10 aaattccct actctaaact aataaatcaa                                        30

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
gtggtgggat gtagtta                                                     17

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
gggttggtgg tgtaggatat a                                                21

<210> SEQ ID NO 13
<211> LENGTH: 30
<212> TYPE: DNA
<213> ORGANISM: Artificial Sequence

```
<220> FEATURE:
<223> OTHER INFORMATION: Primer

<400> SEQUENCE: 13
aacccatcct acccaaatcc taataattaa                                30

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ataattaaaa aaccacccct a                                         21

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
gttggtagag tgttggtagg atata                                     25

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
cctccaaaac cccaaaaacc aacctatc                                  28

<210> SEQ ID NO 17
<211> LENGTH: 16
<212> TYPE: DNA
<213> ORGANISM: Artificial Sequence
<220> FEATURE:
<223> OTHER INFORMATION: Primer

<400> SEQUENCE: 17
ggggttgttt aggtta                                               16

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
tttatgggaa gggggagg                                             18

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
ccccacccca cttaacctt                                            19
```

```
<210> SEQ ID NO 20
<211> LENGTH: 17
<212> TYPE: DNA
<213> ORGANISM: Artificial Sequence
<220> FEATURE:
<223> OTHER INFORMATION: Primer

<400> SEQUENCE: 20
cccacttaac cttaact                                                    17

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
atggtttagg ggggttaaag t                                               21

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
caacccctcc cccttcccat                                                 20

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
agtagagtta ggtttagga                                                  19

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
ttggagaatt tgatggagat tgaagttaa                                       29

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
actatccctc ccaacctta                                                  19

<210> SEQ ID NO 26
<211> LENGTH: 25
<212> TYPE: DNA
<213> ORGANISM: Artificial Sequence
<220> FEATURE:
<223> OTHER INFORMATION: Primer
```

```
<400> SEQUENCE: 26
tttttttgaa attttatgat ttagt                                    25

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
tttagtttag gttggttatt ttagtgag                                 28

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
cacccctccc acaatcaata aattaactt                                29

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
attttagtga gaggttgtat                                          20

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
gtttttgggt tgggtgttta ttag                                     24

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
ccaacaacaa cactaaacca tacatat                                  27

<210> SEQ ID NO 32
<211> LENGTH: 15
<212> TYPE: DNA
<213> ORGANISM: Artificial Sequence
<220> FEATURE:
<223> OTHER INFORMATION: Primer

<400> SEQUENCE: 32
gttttggtgg tgggg                                               15

<210> SEQ ID NO 33
```

```
<211> LENGTH: 27
<212> TYPE: DNA
<213> ORGANISM: Artificial Sequence
<220> FEATURE:
<223> OTHER INFORMATION: Primer

<400> SEQUENCE: 33
tttaggggtt ttgttgatag ggggaag                                        27

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
acctctaaat ctcccacaat ttca                                           24

<210> SEQ ID NO 35
<211> LENGTH: 15
<212> TYPE: DNA
<213> ORGANISM: Artificial Sequence
<220> FEATURE:
<223> OTHER INFORMATION: Primer

<400> SEQUENCE: 35 ataggggaa gtttg                                                      15

<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36
tgaagaaata gagggttttt agtagga                                        27

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37
ttcactacaa ccaaaaaaaa actcattta                                      29

<210> SEQ ID NO 38
<211> LENGTH: 17
<212> TYPE: DNA
<213> ORGANISM: Artificial Sequence
<220> FEATURE:
<223> OTHER INFORMATION: Primer

<400> SEQUENCE: 38
tttgttgtgg gtatagg                                                   17

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
```

-continued

```
aatgagtttt tttttggttg tagtgaat                                28

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
cccctatatc ctaccaacac t                                       21

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41 tttttggtt gtagtgaatt                                          20

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
gtggggattg tttatttttg agag                                    24

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
aacctatccc ctacctcc                                           18

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
attgtttatt tttgagaggg ta                                      22

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
gttttgggag tggttttggt ag                                      22

<210> SEQ ID NO 46
<211> LENGTH: 28
<212> TYPE: DNA
```

```
<213> ORGANISM: Artificial Sequence
<220> FEATURE:
<223> OTHER INFORMATION: Primer

<400> SEQUENCE: 46
cccaaccacc ccaattaccc ataataaa                                              28

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gtagggtttt tttttgtaga                                                       20

<210> SEQ ID NO 48
<211> LENGTH: 26
<212> TYPE: DNA
<213> ORGANISM: Artificial Sequence
<220> FEATURE:
<223> OTHER INFORMATION: Primer

<400> SEQUENCE: 48
ttgttggttt agttgtgttt tgtaag                                                26

<210> SEQ ID NO 49
<211> LENGTH: 28
<212> TYPE: DNA
<213> ORGANISM: Artificial Sequence
<220> FEATURE:
<223> OTHER INFORMATION: Primer

<400> SEQUENCE: 49
cccaaccacc ccaattaccc ataataaa                                              28

<210> SEQ ID NO 50
<211> LENGTH: 17
<212> TYPE: DNA
<213> ORGANISM: Artificial Sequence
<220> FEATURE:
<223> OTHER INFORMATION: Primer

<400> SEQUENCE: 50
gttgtgtttt gtaaggg                                                          17

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
tgttggttta gttgtgtttt gtaag                                                 25

<210> SEQ ID NO 52
<211> LENGTH: 18
<212> TYPE: DNA
<213> ORGANISM: Artificial Sequence
<220> FEATURE:
<223> OTHER INFORMATION: Primer

<400> SEQUENCE: 52
caaccccaat ctcctcct                                                         18
```

```
<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
tttatttatt tattatgggt aattg                                              25

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
aggagattgg ggttggaga                                                     19

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
accaccacct ccccaaatcc                                                    20

<210> SEQ ID NO 56
<211> LENGTH: 15
<212> TYPE: DNA
<213> ORGANISM: Artificial Sequence
<220> FEATURE:
<223> OTHER INFORMATION: Primer

<400> SEQUENCE: 56
ggatgggggt ttttt                                                         15

<210> SEQ ID NO 57
<211> LENGTH: 18
<212> TYPE: DNA
<213> ORGANISM: Artificial Sequence
<220> FEATURE:
<223> OTHER INFORMATION: Primer

<400> SEQUENCE: 57
agattggggt tggagagg                                                      18

<210> SEQ ID NO 58
<211> LENGTH: 18
<212> TYPE: DNA
<213> ORGANISM: Artificial Sequence
<220> FEATURE:
<223> OTHER INFORMATION: Primer

<400> SEQUENCE: 58
cccacttccc ccctactt                                                      18

<210> SEQ ID NO 59
<211> LENGTH: 15
<212> TYPE: DNA
<213> ORGANISM: Artificial Sequence
<220> FEATURE:
```

<223> OTHER INFORMATION: Primer

<400> SEQUENCE: 59
aaaccaacca aacct                                                    15

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
ggagattggg gttggaga                                                 18

<210> SEQ ID NO 61
<211> LENGTH: 18
<212> TYPE: DNA
<213> ORGANISM: Artificial Sequence
<220> FEATURE:
<223> OTHER INFORMATION: Primer

<400> SEQUENCE: 61
cccacttccc ccctactt                                                 18

<210> SEQ ID NO 62
<211> LENGTH: 17
<212> TYPE: DNA
<213> ORGANISM: Artificial Sequence
<220> FEATURE:
<223> OTHER INFORMATION: Primer

<400> SEQUENCE: 62
aggtttggtt ggtttta                                                  17

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
tggtttgatg gggagtaggt taa                                           23

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64
tccacctact aatcaaaata attcacactt                                    30

<210> SEQ ID NO 65
<211> LENGTH: 16
<212> TYPE: DNA
<213> ORGANISM: Artificial Sequence
<220> FEATURE:
<223> OTHER INFORMATION: Primer

<400> SEQUENCE: 65
tggggagtag gttaat                                                   16

```
<210> SEQ ID NO 66
<211> LENGTH: 19
<212> TYPE: DNA
<213> ORGANISM: Artificial Sequence
<220> FEATURE:
<223> OTHER INFORMATION: Primer

<400> SEQUENCE: 66
ggtttagtgg ggagtgagg                                              19

<210> SEQ ID NO 67
<211> LENGTH: 30
<212> TYPE: DNA
<213> ORGANISM: Artificial Sequence
<220> FEATURE:
<223> OTHER INFORMATION: Primer

<400> SEQUENCE: 67 tatccccctca aacaaatact accttaccac                                 30

<210> SEQ ID NO 68
<211> LENGTH: 19
<212> TYPE: DNA
<213> ORGANISM: Artificial Sequence
<220> FEATURE:
<223> OTHER INFORMATION: Primer

<400> SEQUENCE: 68
agggttgtgt tttttaat                                               19
```